(12) United States Patent
Gould et al.

(10) Patent No.: US 7,056,491 B2
(45) Date of Patent: Jun. 6, 2006

(54) MONOTERPENES AND SESQUITERPENES AS CHEMOTHERAPEUTIC AND RADIATION SENSITIZERS AND IMMUNOMODULATORS

(75) Inventors: Michael N. Gould, Madison, WI (US); Steven P. Howard, Madison, WI (US); Deepika Rajesh, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 21 days.

(21) Appl. No.: 10/014,724

(22) Filed: Nov. 7, 2001

(65) Prior Publication Data

US 2002/0137799 A1    Sep. 26, 2002

Related U.S. Application Data

(63) Continuation-in-part of application No. 09/878,797, filed on Jun. 11, 2001, now abandoned.

(60) Provisional application No. 60/246,887, filed on Nov. 8, 2000.

(51) Int. Cl.
*A61K 49/00* (2006.01)
(52) U.S. Cl. ...................... 424/9.1; 424/1.11; 424/1.65
(58) Field of Classification Search ............... 424/1.11, 424/1.65, 9.1, 9.2; 585/350; 514/1; 544/313
See application file for complete search history.

(56) References Cited

U.S. PATENT DOCUMENTS

| 5,587,402 | A * | 12/1996 | Gould et al. | 514/729 |
| 5,602,184 | A * | 2/1997 | Myers et al. | 514/739 |
| 2002/0054850 | A1* | 5/2002 | Gould et al. | 424/1.11 |
| 2003/0054052 | A1* | 3/2003 | Haridas et al. | 424/757 |
| 2003/0125373 | A1* | 7/2003 | Nakshatri et al. | 514/449 |

FOREIGN PATENT DOCUMENTS

WO    WO 94/20080    9/1994

OTHER PUBLICATIONS

Rajesh, D. et al., Perillyl Alcohol as a Radiosensitizer in Malignant Gliomas, abstract of presentation made at SNO Meeting (11/12/2000), Chicago.
Boesen-De-Cock, Jeanine G.R., et. al., Common Regulation of Apoptosis Signaling Induced by CD95 and the DNA-damaging Stimuli Etoposide and -Radiation Downstream from Caspase-8 Activation, Journal of Bio. Chem., 274:20, Issue of May 14, 14255-14261, 1999.
Duan, Lian et al., Sensitization of Human Malignant Glioma Cell Lines to Tumor Necrosis Factor-Induced Apoptosis by Cisplatin, Journal of Neuro-Oncology 52:23-36, 2001.
Fulda, Simone et al., The CD95 (APO-1/Fas) System Mediates Drug-Induced Apoptosis in Neuroblastoma Cells, Cancer Research 57, 3823-3829, Sep. 1, 1997.
Fulda, Simone et al., Activation of the CD95 (APO-1/Fas) Pathway in Drug- and-Irradiation-induced Apoptosis of Brain Tumor Cells, Cell Death and Differentiation (1998) 5, 884-893.
Green, Douglas R., Apoptotic Pathways: The Roads to Ruin, Cell 94:695-698, Sep. 18, 1998.
Herr, Ingrid et al., Activation of CD95 (APO-1/Fas) Signaling by Ceramide Mediates Cancer Therapy-Induced Apoptosis, EMBO Journal 16:20, 6200-6208, 1997.
Houghton, Janet A. et al., The Fas Signaling Pathway is Functional in Colon Carcinoma Cells and Induces Apoptosis, Clin. Cancer Res. 3:2205-2209, Dec. 1997.
Kimura, Kotohiko et al., Tumor Necrosis Factor- and Fas Activate Complementary Fas-associated Death domain-dependent Pathways that Enhance Apoptosis Induced by-Irradiation, Journ. Biol. Chem., 275:12, Iss. Of Mar. 24, 8610-8617, 2000.
Li, Jie-Hui et al., The Regulation of CD95 Ligand Expression and Function in CTL, American Association of Immunologists 3943-3949, 1998.
Micheau, Olivier et al., Sensitization of Cancer Cells Treated with Cytotoxic Drugs to Fas-Mediated Cytotoxicity, J. Nat. Cancer Inst. 89:11, Jun. 4, 1997.
Mizutani, Youichi et al., Doxorubicin Sensitizes Human Bladder Carcinoma Cells to Fas-Mediated Cytotoxicity, Cancer 79:6, 1180-1189, Mar. 15, 1997.
Mueller, Martina et al., p53 Activates the CD95 (APO-1/Fas) Gene in Response to DNA Damage by Anticancer Drugs, J. Exp. Med. 188:11, Dec. 7, 1998, 2033-2045.
Nagata, Shigekazu, Fas Ligand-Induced Apoptosis, Annu. Rev. Genet. 1999, 33:29-55.
O'Connor, Liam et al., CD95 (Fas/APO-1) and p53 Signal Apoptosis Independently in Diverse Cell Types, Cancer Res. 60, 1217-1220, Mar. 1, 2000.
Pinkoski, M.J. and Green, D.R., Fas Ligand, Death Gene, Cell Death and Differentiation (1999) 6, 1174-1181.
Rokhlin, Oskar W., et al., Fas-Mediated Apoptosis in Human Prostatic Carcinoma Cell Lines Occurs Via Activation of Caspase-8 and Caspase-7, Cancer Research 58, 5870-5875, Dec. 15, 1998.
Roth, W. et al., Taxol-Mediatied Augmentation of CD95 Ligand-Induced Apoptosis of Human Malignant Glioma Cells: Association with bcl-2 Phosphorylation but Neither Activation of p53 nor G /M Cell Cycle Arrest, British J. of Cancer (1998) 77(3):404-411.

(Continued)

Primary Examiner—Dameron L. Jones
(74) Attorney, Agent, or Firm—Quarles & Brady, LLP

(57) ABSTRACT

A method of sensitizing tumor cells to radiation thereapy, chemotherapy and immunomodulatory thereapy, comprising the step of exposing the tumor cell to an effective amount of at least one monoterpene or sesquiterpene and treating the tumor cell is disclosed.

20 Claims, 30 Drawing Sheets

OTHER PUBLICATIONS

Roth, Wilfried et al., Interferon- Enhances CD95L-Induced Apoptosis of Human Malignant Glioma Cells, J. of Neuroimmun. 87 (1998) 121-129.

Weller, Michael, CD95 Ligand: Lethal Weapon Against Malignant Glioma? Brain Path. 8:285-293 (1998).

Wu, Xiu-Xian, Enhancement of Fas-Mediated Apoptosis in Renal Cell Carcinoma Cells in Adriamycin, Cancer Res. 60, 2912-2918, Jun. 1, 2000.

Yount, Garret L., Fas (APO-1/CD95) Signaling Pathway is Intact in Radioresistant Human Glioma Cells, Cancer Res., 59, 1362-1365, Mar. 15, 1999.

Zagury, Daniel, Toward a New Generation of Vaccines: the Anti-Cytokine Therapeutic Vaccines, PNAS 98:14 8024-8029, Jul. 3, 2001.

M. Mehta, et al., "Brain Tumor Committee," Int. J. Radiation Oncology Biol. Phys. 51(3):11-18, 2001.

A. C. Miller and D. Samid, "Tumor Radiosensitization Based on the Use of Inhibitors of the Mevalonate Pathway of Cholesterol Synthesis," Eicosanoids and Other Bioactive Lipids in Cancer Inflammation and Radiation Injury 2, Edited by K.V. Honn et al, 1997, pp. 825-830.

Broitman SA, et al., "Effects of monoterpenes and mevinolin on murine colon tumor CT-26 in vitro and its hepatic 'metastases' in vivo," Adv. Exp. Med. Biol. 401:111-130, 1996.

Chen Y and Hu D, "Effects of POH in combination with ST1571 on the proliferation and apoptosis of K562 cells," J. Huazhon Univ. Sci. Technolog. Med. Sci. 24(1):41-44, 2004.

Hyer ML, et al., "Synthetic triterpenoids cooperates with tumor necrosis factor-related apoptosis-inducing ligand to induce apoptosis of breast cancer cells," Cancer Res. 6541), 4799-4808, 2005.

Keane MM, et al., "Chemotherapy augments TRAIL-induced apoptosis in breast cell lines," Cancer Res. 59(3):734-741, 1999.

Mo H and Elson CE, "Studies of the isoprenoid-mediated inhibition of mevalonate synthesis applied to cancer chemotherapy and chemoprevention," Exp. Biol. Med. 229:567-585, 2004.

Rajesh D, et al., "Perillyl alcohol as a radio-/chemosensitizer in malignant glioma," J. Biol. Chem. 278(38):35968-35978, 2003.

Shi B, et al., "The farnesyl protein transferase inhibitor SCH66336 synergizes with taxanes in vitro and enhances their antitumor activity in vivo," Cancer Chemother. Pharmacol 46:387-393. 2000.

Vigushin DM, et al., "Phase I and pharmacokinetic study of D-limonene in patients with advanced cancer. Cancer Research Campaign Phase I/II Clinical Trials Committee," Cancer Chemother Pharmacol 42(2):111-117 1998.

Yu D, "Mechanisms of ErbB2-mediated paclitaxel resistance and trastuzumab-mediated paclitaxel sensitization in ErbB2-overexpressing breast cancers," 28(Suppl. 16):12-17, 2001.

Zhang S, et al., "Anti-cancer potential of sesquiterpene lactones: bioactivity and molecular mechanisms," Curr. Med. Chem. Anti-Canc. Agents 5(3):239, 2005.

International Agency for Research on Cancer IARC—Summaries & Evaluations, Lumber and Sawmill Industries (Including Logging) (Group 3) Suppl. 7:383, 1987.

* cited by examiner

EFFECT OF PERILLYL ALCOHOL AND RADIATION ON DU145 CELLS

EFFECT OF MYRECENE AND RADIATION ON T98G CELLS

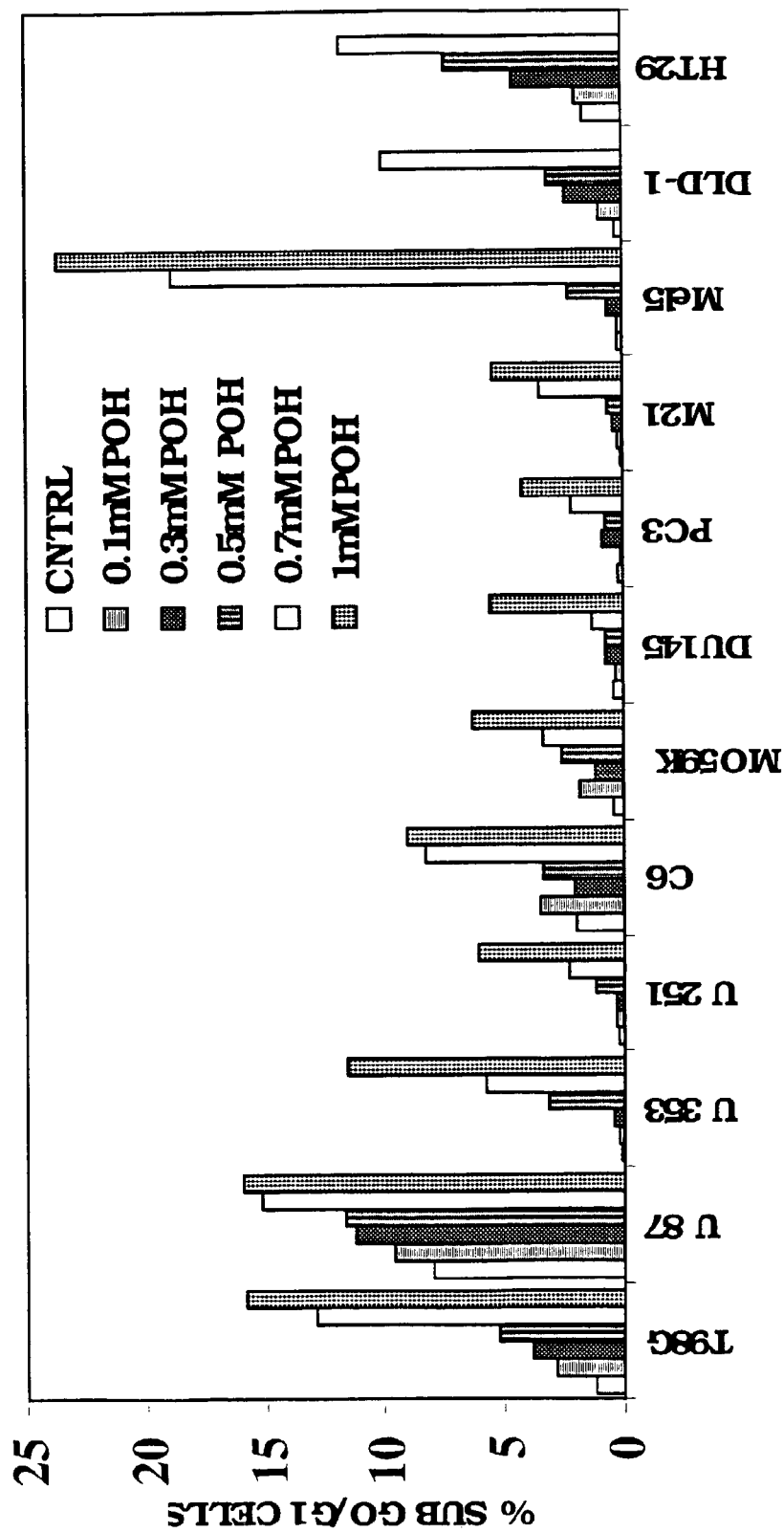
FIG: 15A
EFFECT OF PERILLYL ALCOHOL ON TUMOR CELL LINES

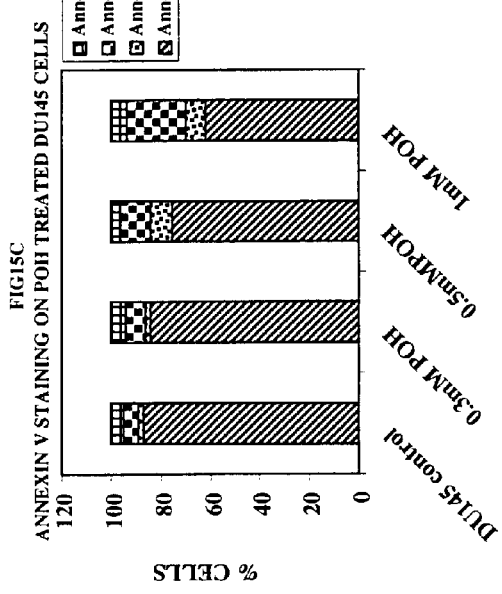
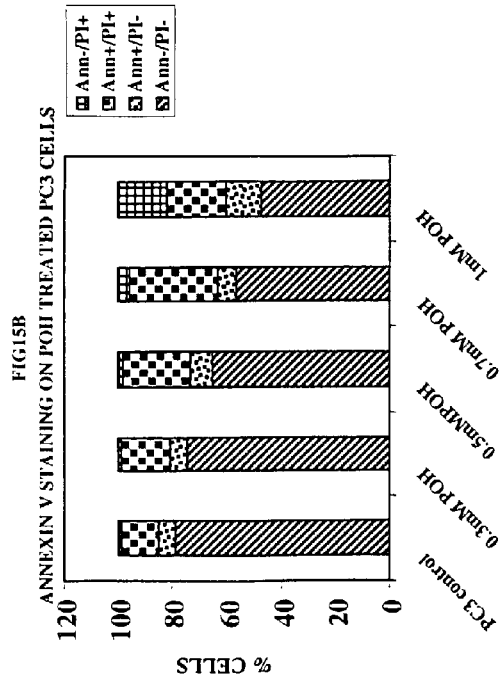
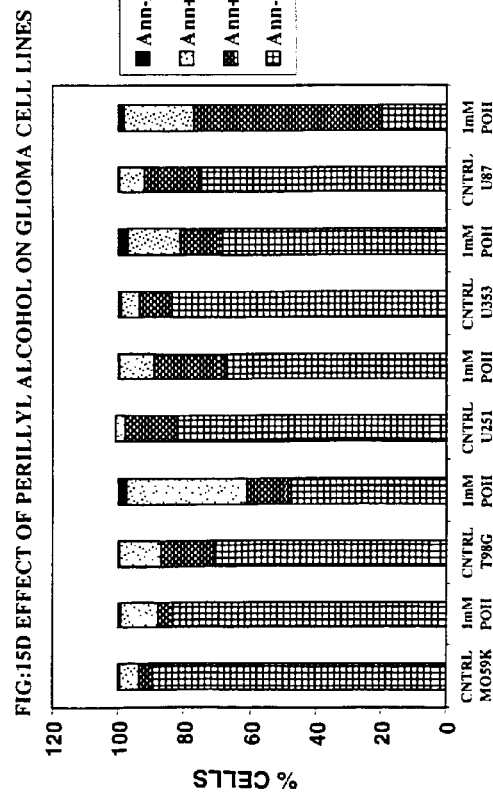

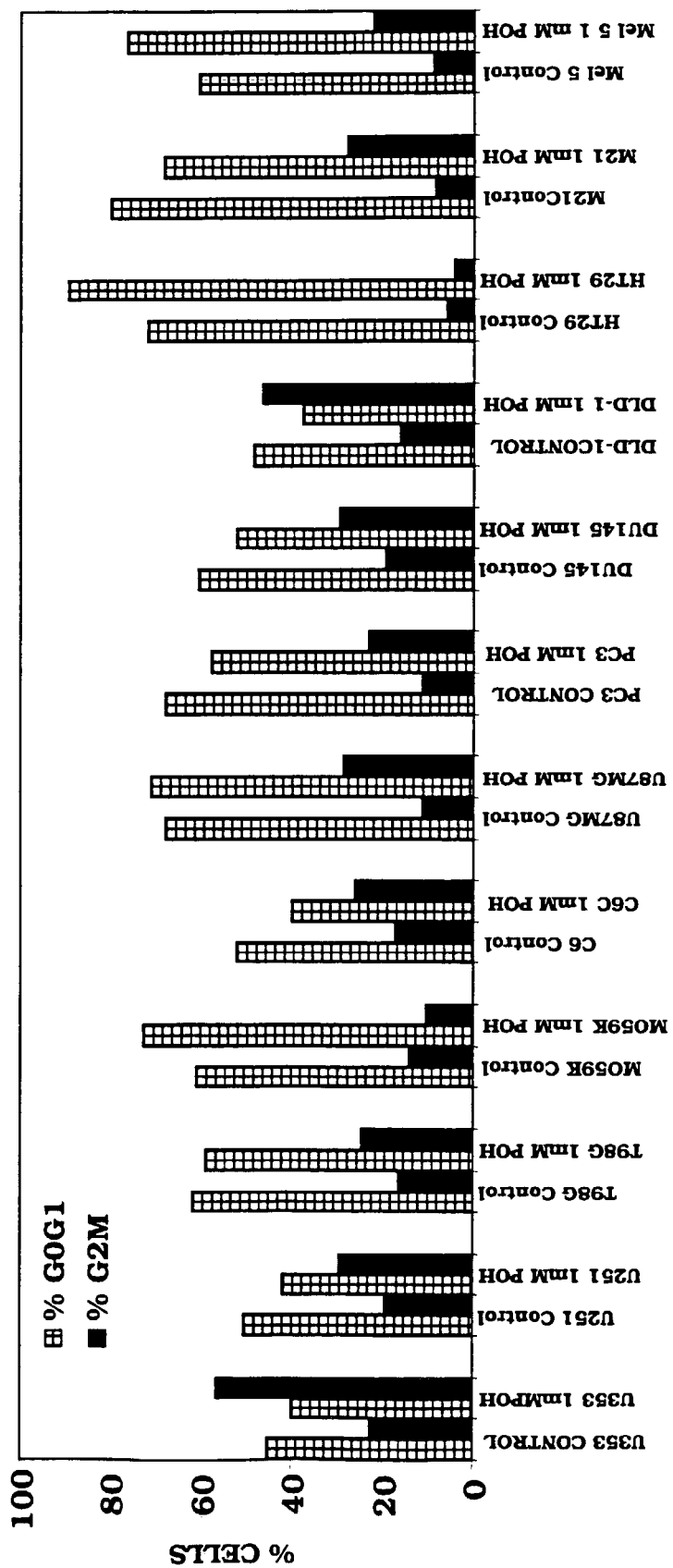

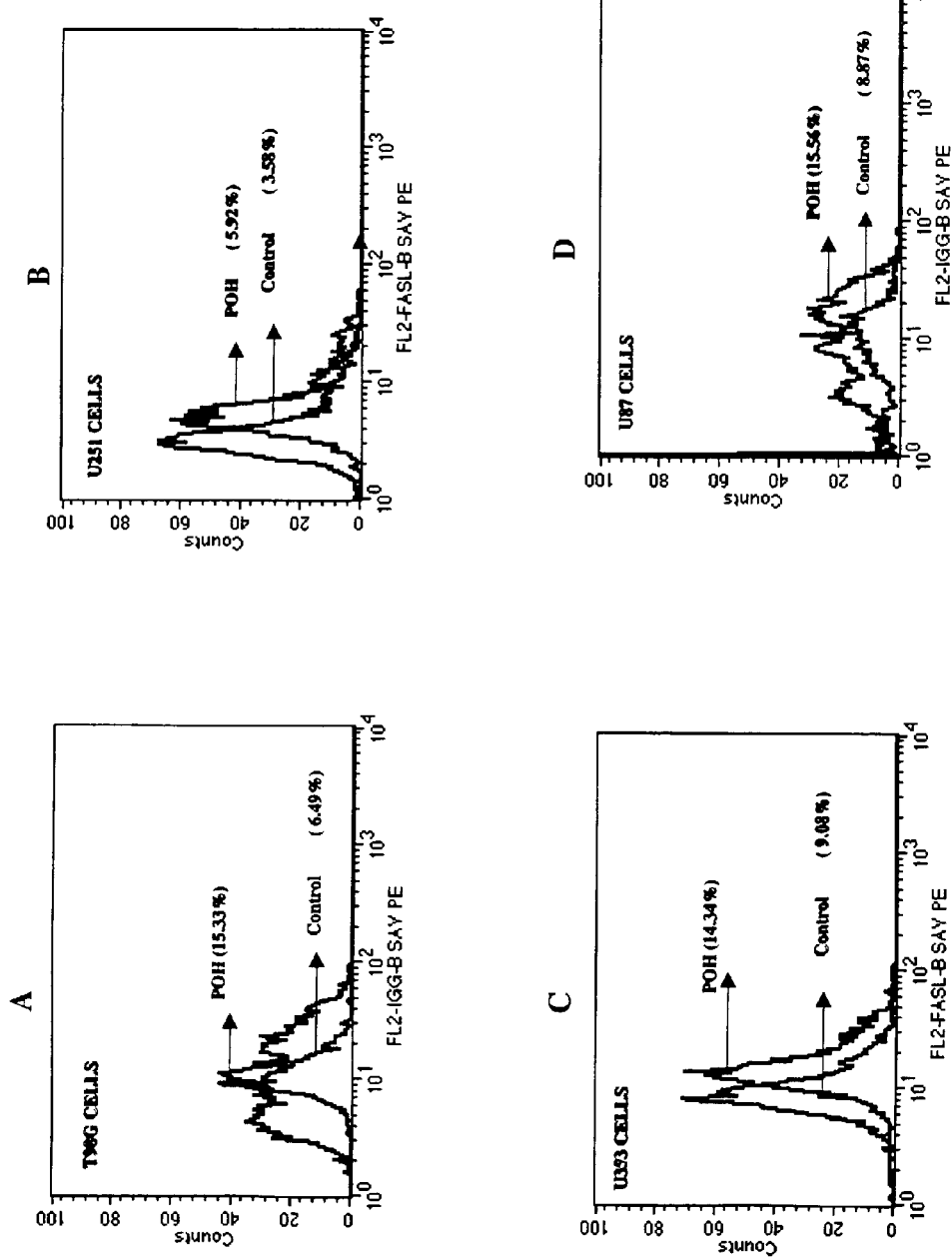
FIG: 17 FAS LIGAND EXPRESSION IN GLIOMA CELLS

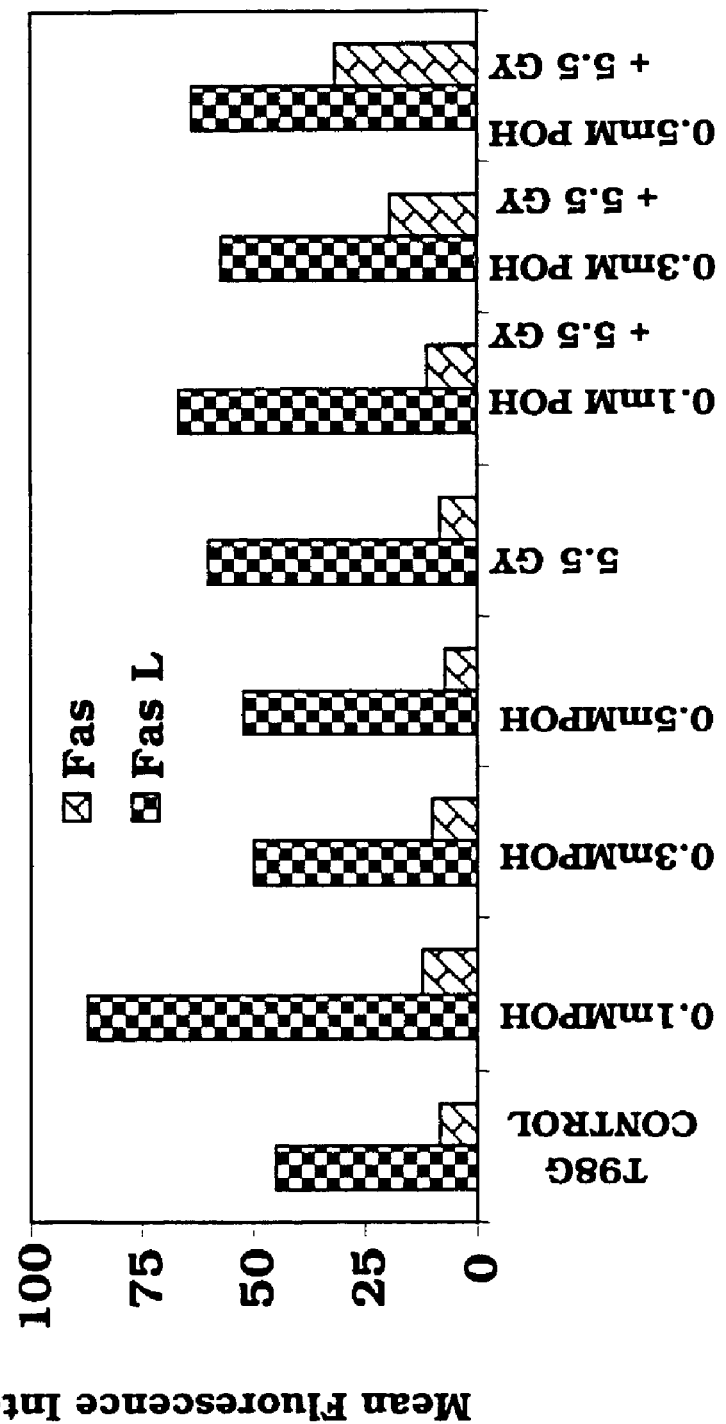
Fig:18
Fas L and Fas expression in T98G cells following Perillyl Alcohol Treatment

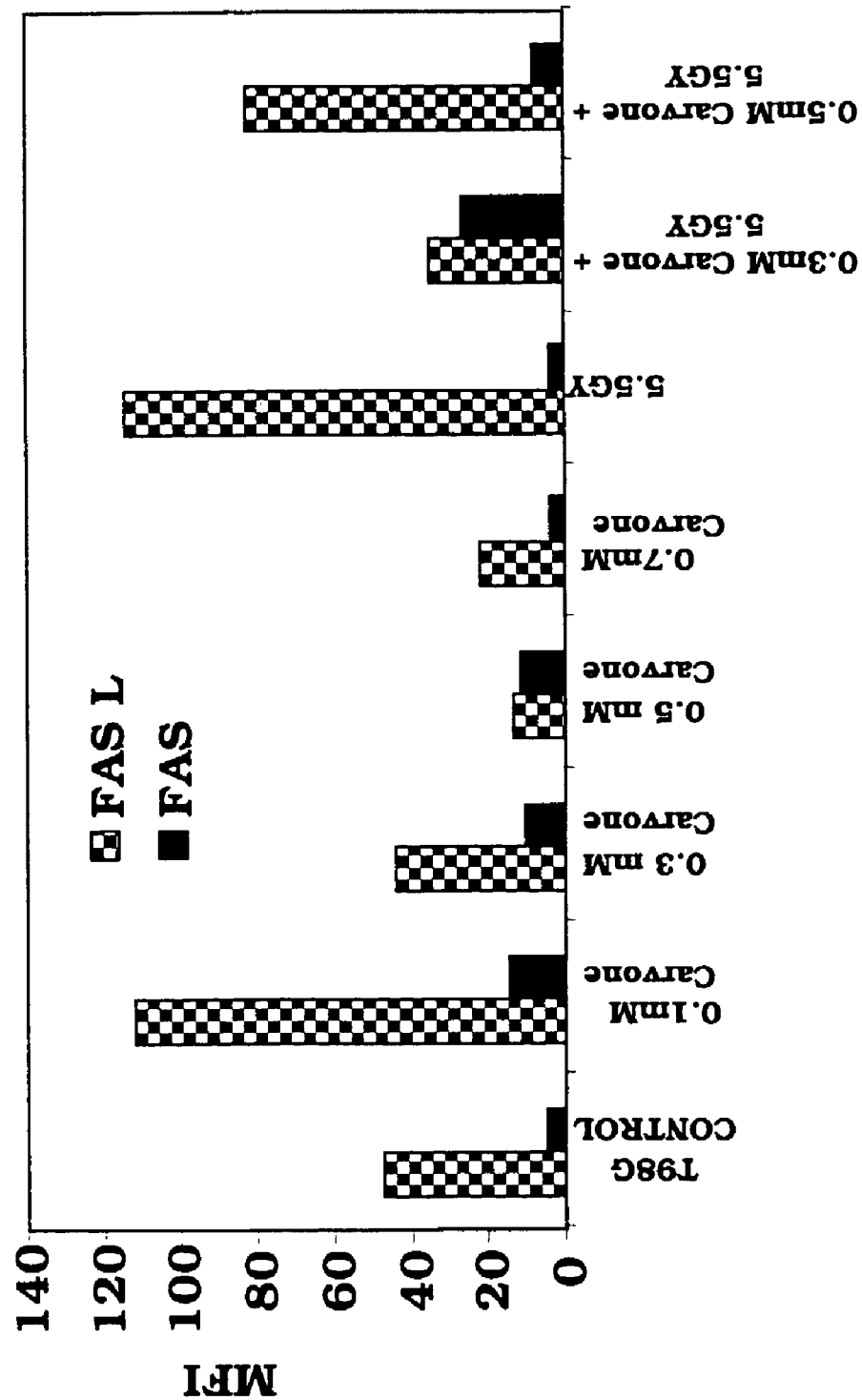
Fig:19
FasL/Fas expression in T98G cells treated with Carvone

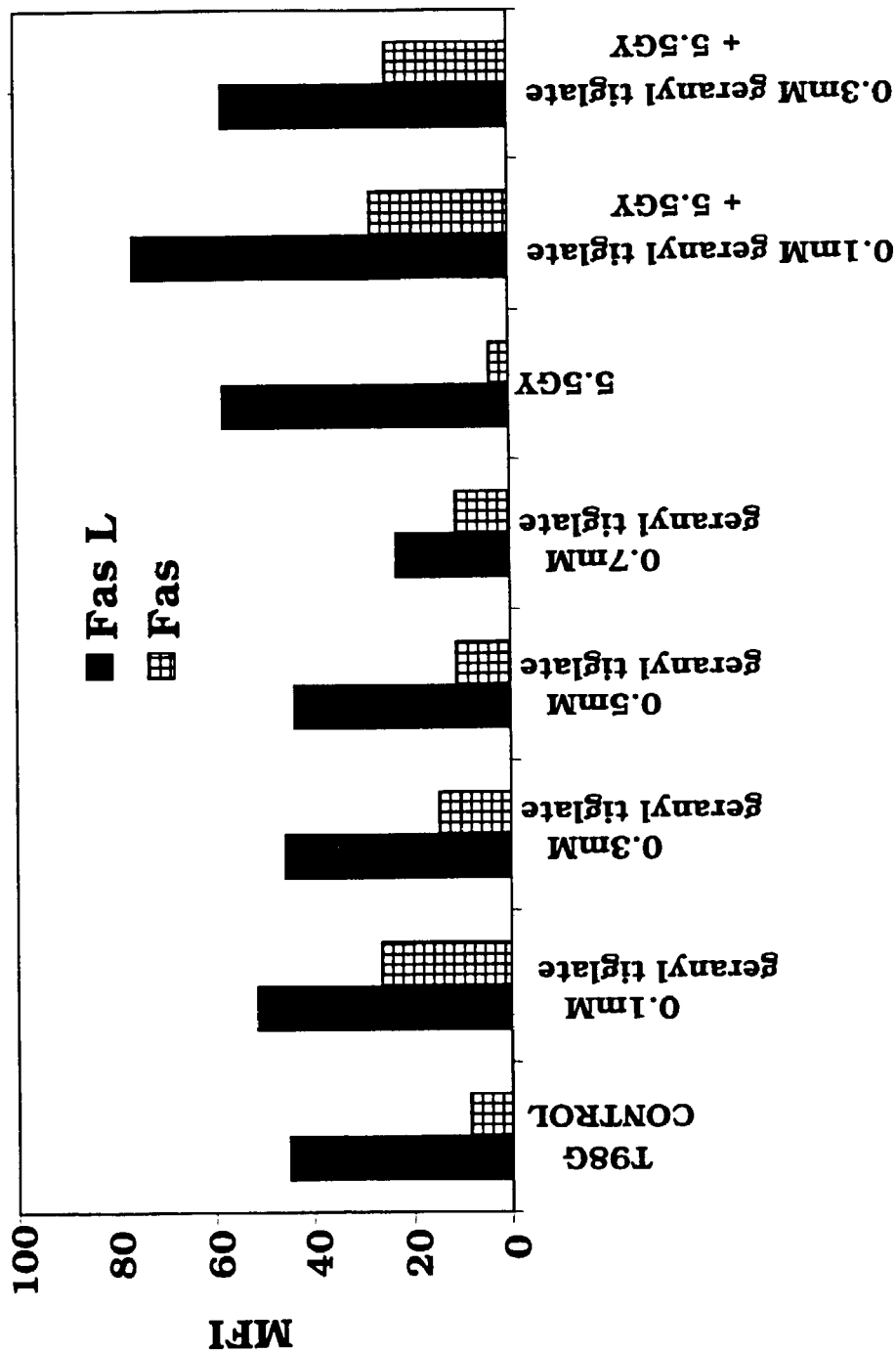
Fig:20
FasL Fas Expression in T98G cells treated with Geranyl Tiglate

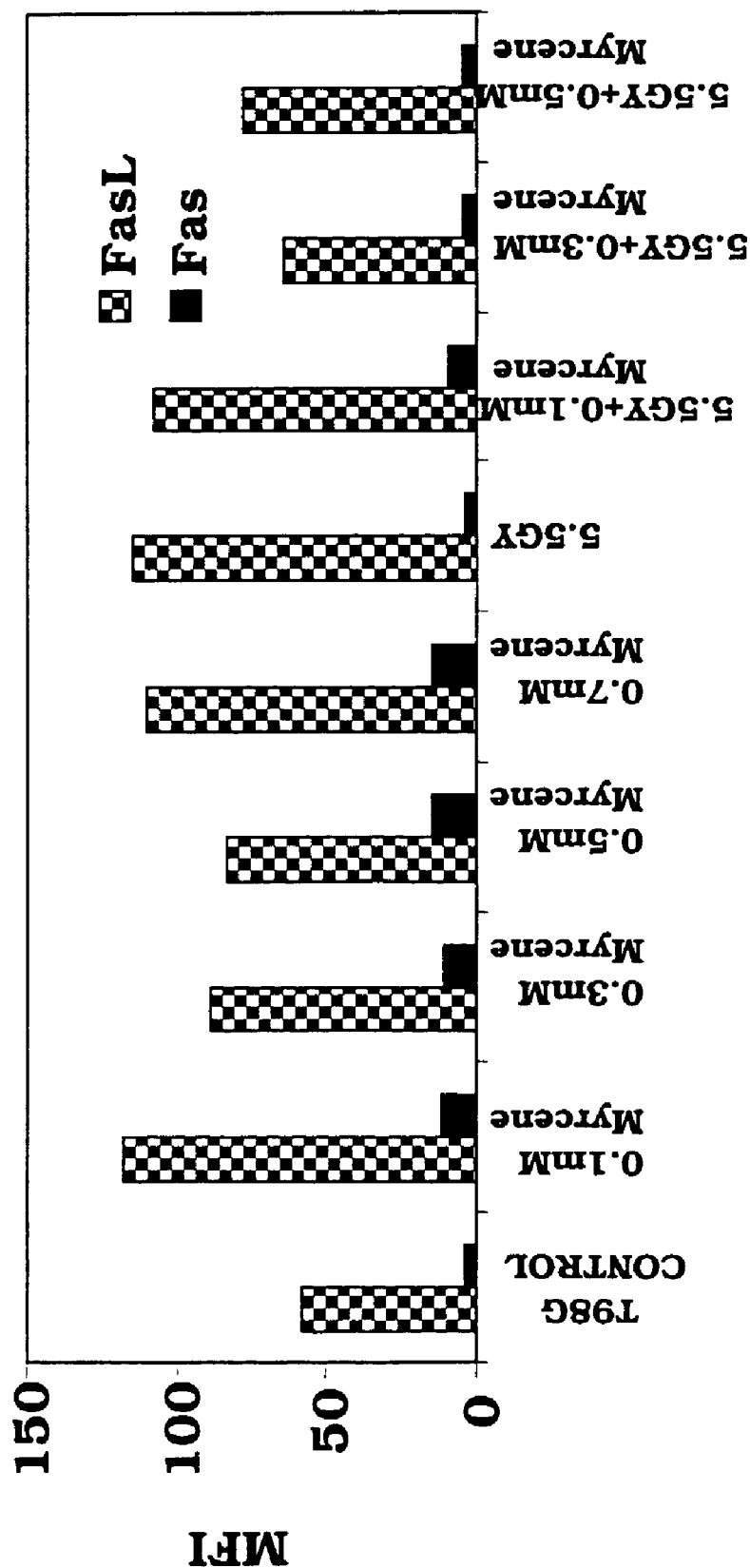
Fig:21
FasL/Fas Expression in T98G cells treated with Myrecene

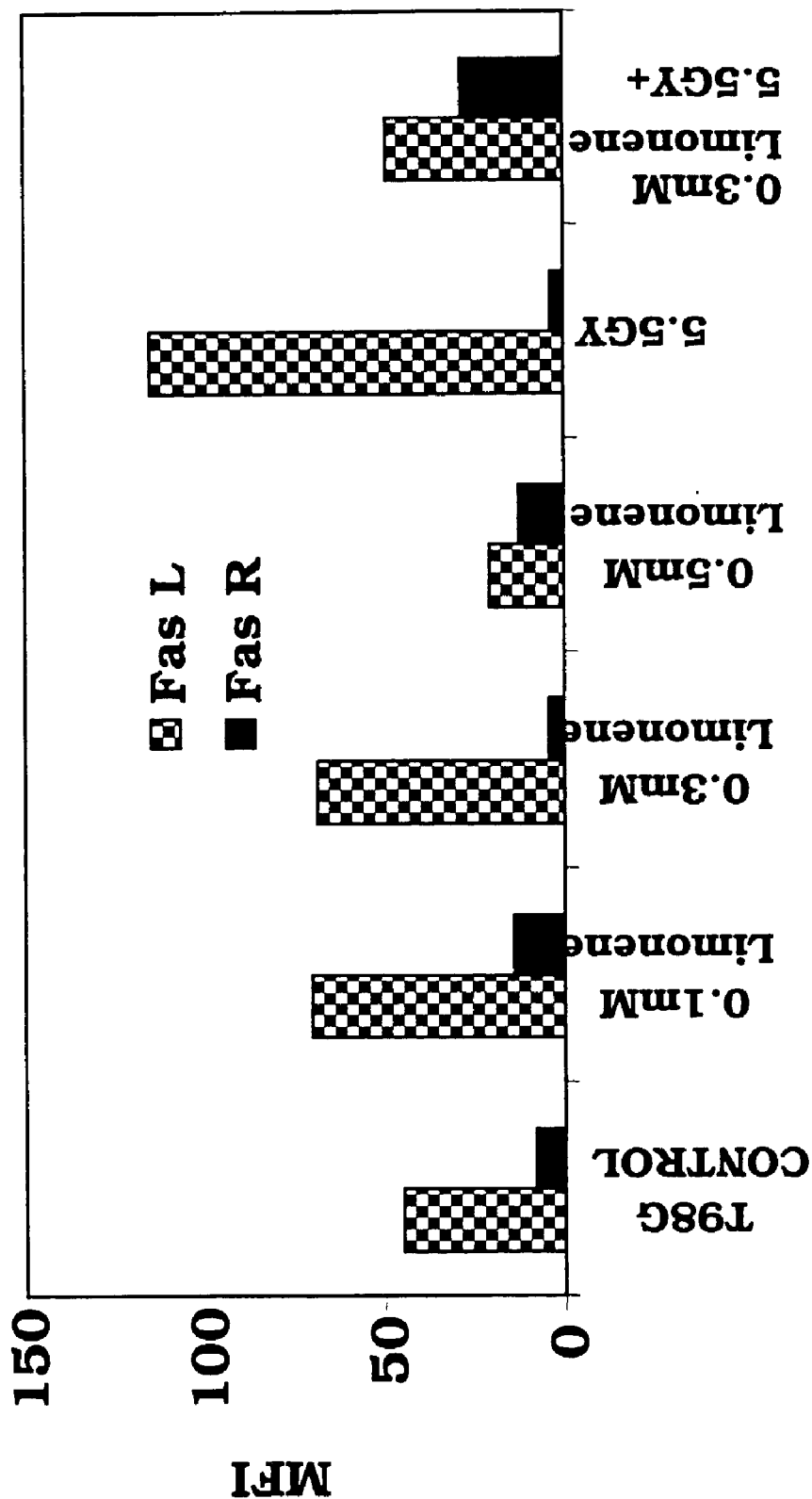

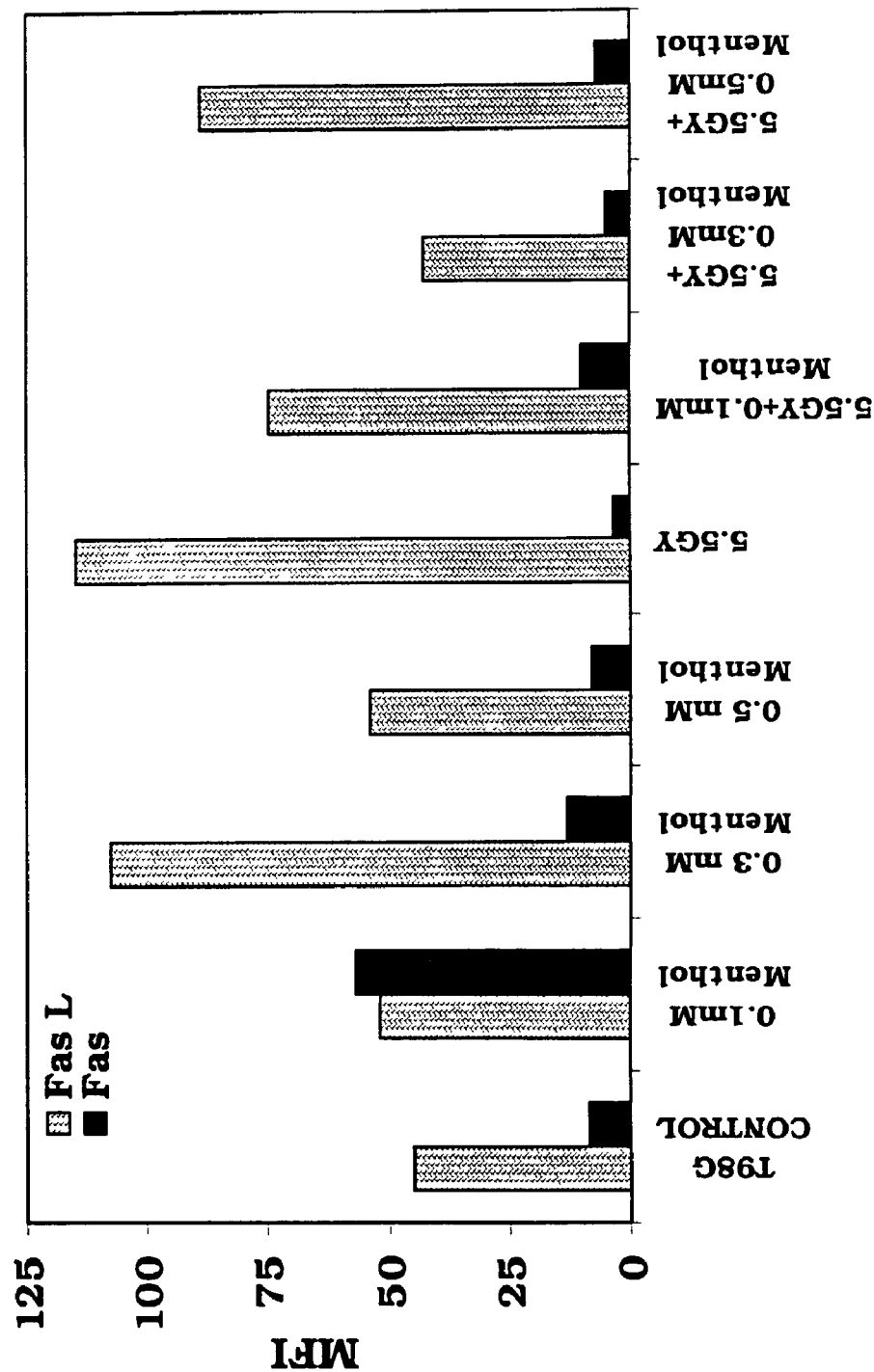
Fig:23
FasL/Fas expression in T98G cells treated with Menthol

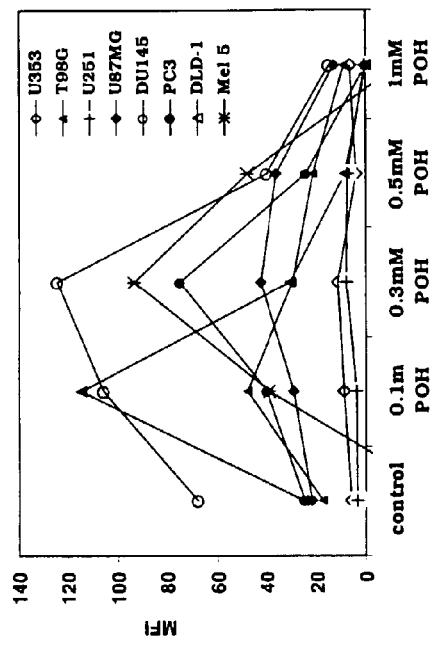
FIG: 24A
POH UPREGULATES FAS L IN TUMOR CELL LINES
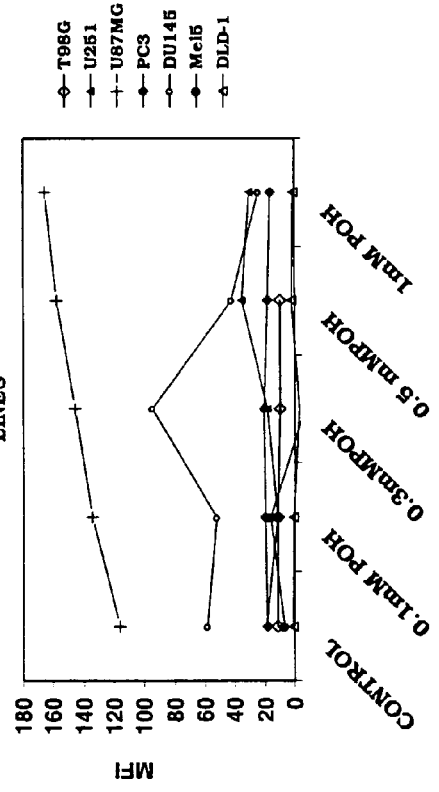
FIG: 24B
POH DOES NOT AFFECT FAS RECEPTOR IN TUMOR CELL LINES

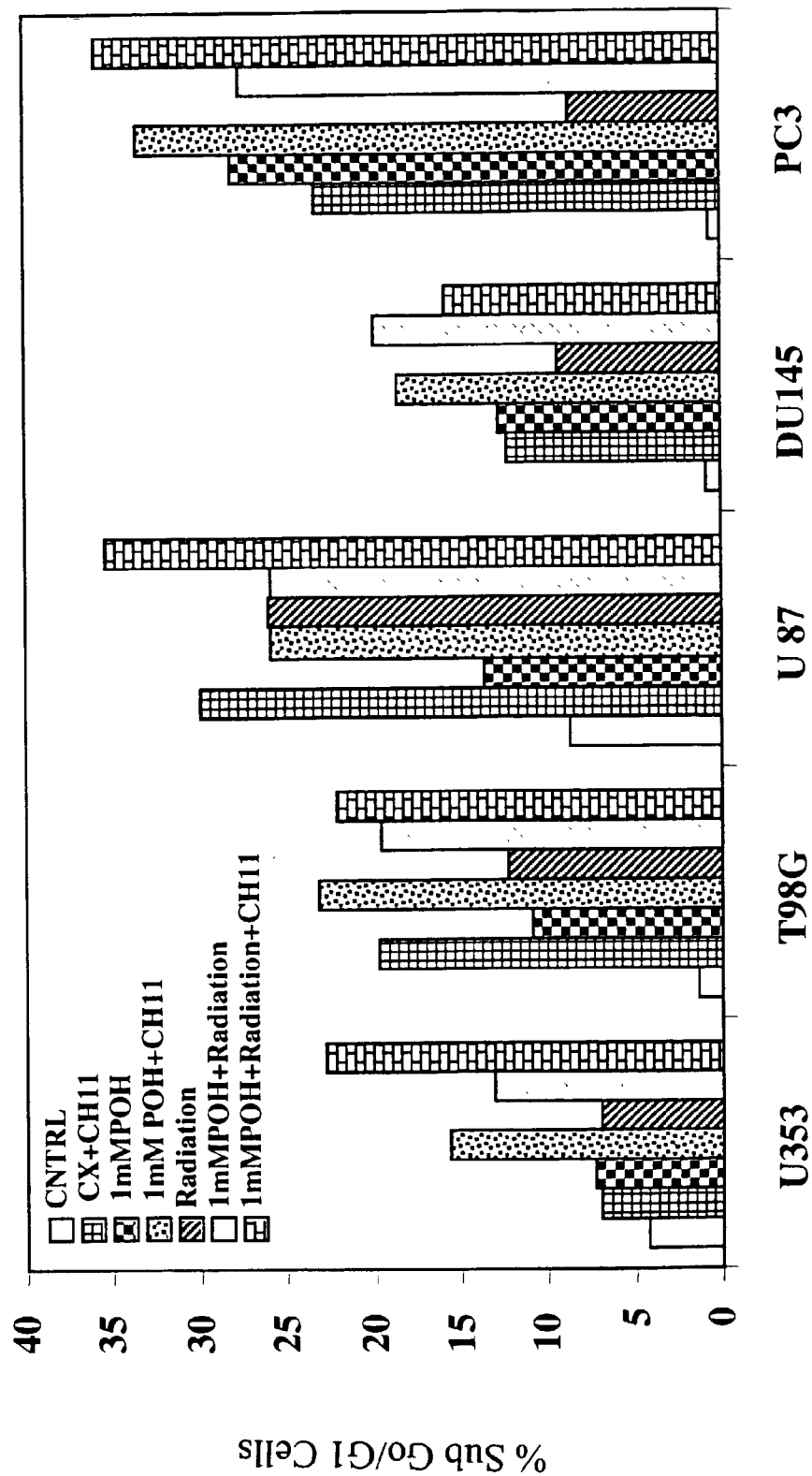

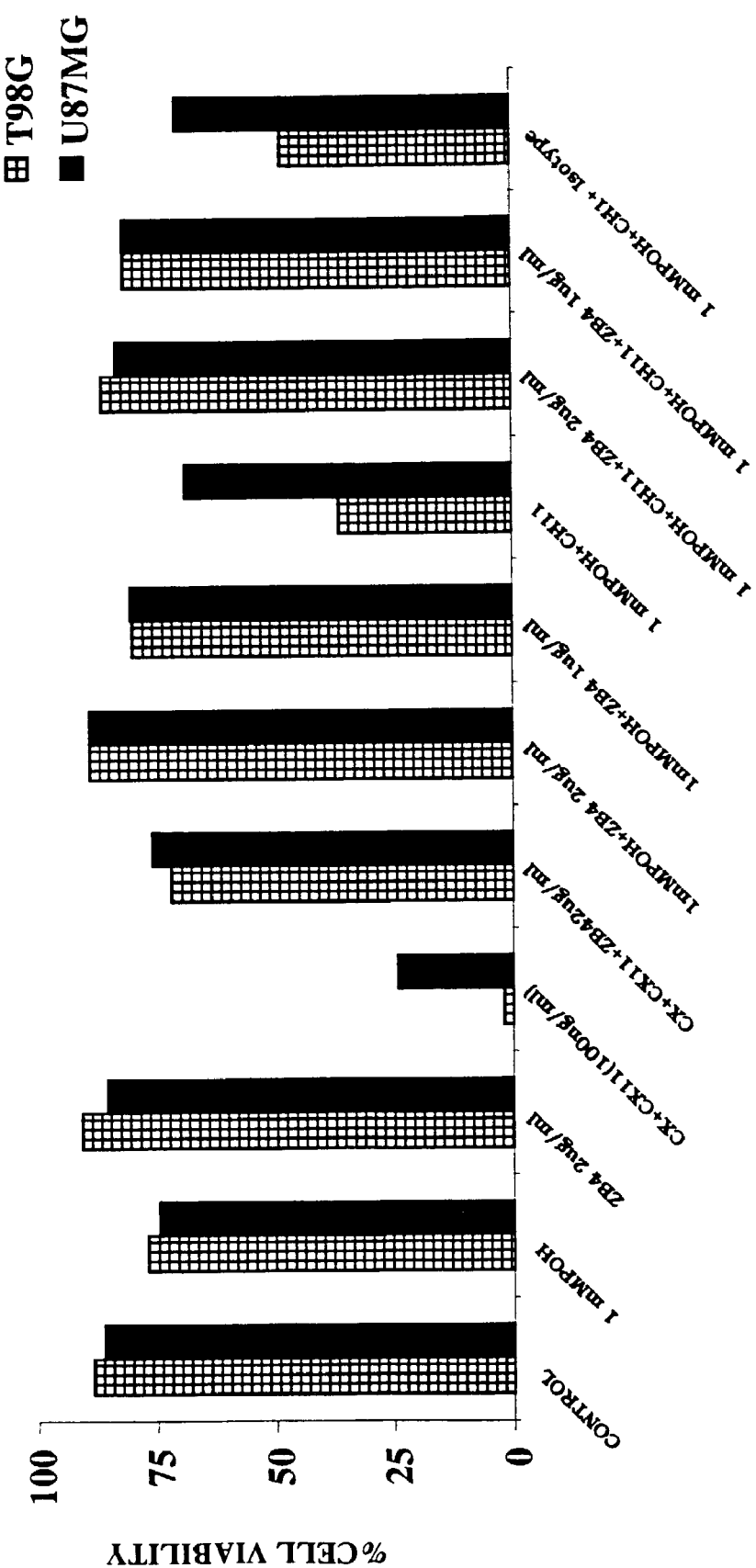
Fig: 26 INHIBITION OF FAS INDUCED APOPTOSIS BY ANTAGONISTIC ANTIBODY (ZB4)

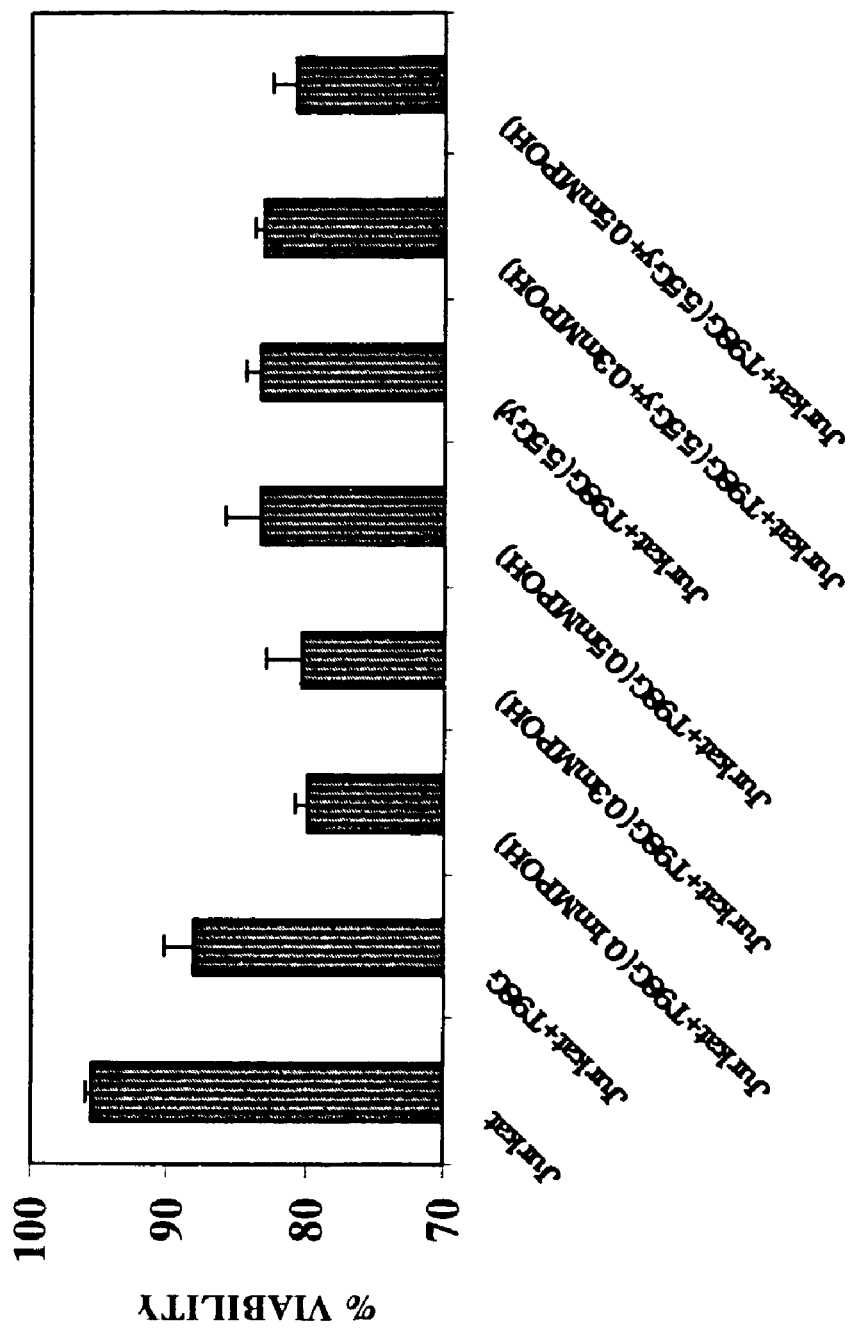

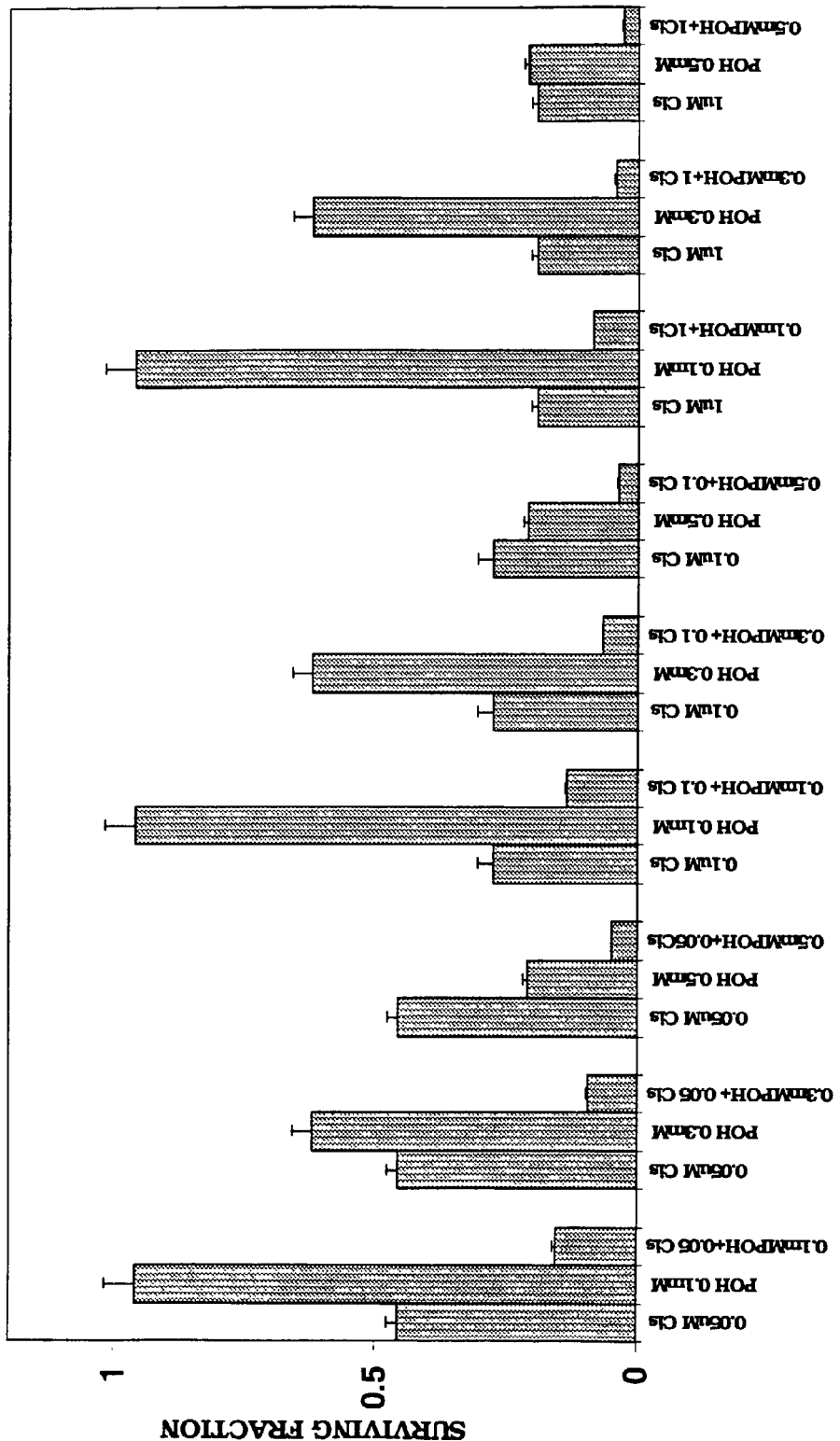
FIG: 28
EEFECT OF CISPLATIN AND POH ON T98G CELLS

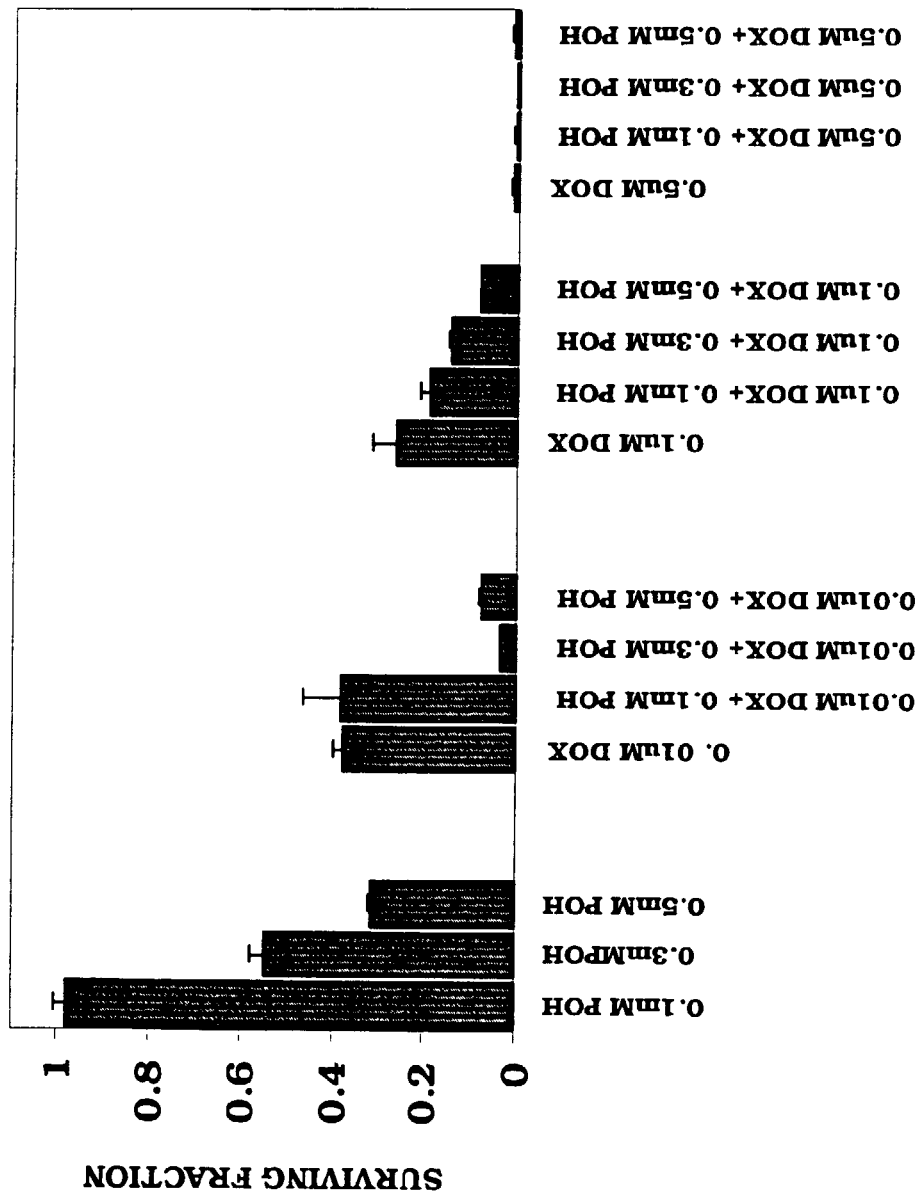
Fig: 29 EFFECT OF DOXORUBICIN AND POH ON T98G CELLS

MONOTERPENES AND SESQUITERPENES AS CHEMOTHERAPEUTIC AND RADIATION SENSITIZERS AND IMMUNOMODULATORS

CROSS-REFERENCE TO RELATED APPLICATION

This application claims priority to provisional patent application Ser. No. 60/246,887, filed Nov. 8, 2000, which is incorporated by reference herein, and is a continuation-in-part of Ser. No. 09/878,797, filed Jun. 11, 2001, now abandoned which is incorporated by reference herein.

STATEMENT REGARDING FEDERALLY SPONSORED RESEARCH OR DEVELOPMENT

BACKGROUND OF THE INVENTION

The incidence of malignant glioma is approximately 12,000 new cases per year. These tumors represent the second leading cause of cancer mortality in people under the age of 35 and the fourth leading cause in those under the age of 54. The exact cause of the disease is unknown, although speculation exists regarding genetic predisposition, chemical, or viral causes. Whatever the cause, recent epidemiological evidence suggests a significant increase in the incidence of these tumors, particularly in the elderly.

The current approach to treatment usually represents a multi-modality approach. Depending upon grade and histopathology, surgery and/or radiation is utilized with or without cytotoxic chemotherapy. For the more advanced types of astrocytoma (Grades III–IV), combined modality approaches have had a questionable impact upon survival; median survival ranges from 40–50 weeks with most patients dead of disease at 2 years.

Despite recent advances in neuro-imaging, neuro-anesthesia, and neuro-surgical techniques, the prognosis of patients with malignant gliomas treated by surgical resection alone remains dismal with a median survival of 4–6 months. This reflects the unique infiltrative growth characteristics of malignant gliomas, which make true "total resection" impossible without causing unacceptable neurologic damage to the patient. To date, radiotherapy has proven to be the most effective treatment for malignant gliomas extending median survival to 8–9 months. Although adjuvant chemotherapy can prolong survival, few patients survive more than 18 months. Furthermore, once patients have tumor progression, conventional chemotherapy has not been shown to prolong survival. There are several reasons why gliomas are relatively resistant to standard chemotherapy including diminished drug delivery to the tumor secondary to the blood-brain barrier, tumor hypoxia, and their relatively low growth fraction. Most importantly, however, is the fact that gliomas tend to have significant intrinsic resistance to most standard cytotoxic agents. Research strategies have been aimed towards the development of new agents directed against novel cellular targets to be used either as single agents or in combination with currently available therapy of proven efficacy.

The development of more effective chemotherapeutic agents intended for combination with radiotherapy such that tumor cell kill is increased while maintaining or improving the therapeutic index has been the clinical rationale for the development of radiosensitizers. Desirable characteristics of clinically useful radiosensitizing agents would include a lack of systemic toxicity and selectivity towards the tumor cell population. Theoretically, the development of an effective radiosensitizer should be particularly appropriate in the management of malignant glioma as 90% of these patients will ultimately develop recurrences within a 2-cm margin of the original tumor, suggesting that these tumors are resistant to standard treatment doses of radiotherapy. In an effort to improve the survival of patients with malignant glioma, numerous clinical studies, both in the single institution and in the larger cooperative group setting evaluating potential radiosensitizers have been conducted. These agents have included halogenated pyrimidine analogs such as bromodeoxyuridine and iododeoxyuridine, hypoxic cell sensitizers such as misonidazole and etanidazole, cytotoxic chemotherapeutic agents such as nitrosoureas, cisplatin, carboplatin and taxol, topoisomerase I inhibitors such as topotecan, inhibitors of protein kinase C such as tamoxifen and biological agents such β-interferon. In spite of this large clinical and laboratory effort to identify effective radiosensitizing agents, the overall survival of patients with malignant glioma has remained unchanged over the last two decades. In addition, one of the key drawbacks of most of these agents is their overwhelming systemic toxicity that often limits their clinical usefulness.

Perillyl alcohol (POH) is a monocyclic monoterpene. Monoterpenes are commonly and primarily produced by plants and are found in many commonly consumed fruits and vegetables, including citrus fruits and food flavoring such as mint. Monoterpenes occur in monocyclic, bicyclic, and acyclic forms and are either simple or modified hydrocarbons. We have demonstrated that sesquiterpenes have activities similar to the monoterpenes. We envision that they act with a similar mechanism.

The potential anticancer activity of limonene was first reported in 1971 by Homburger, et al. who observed that limonene, when co-administered with the carcinogen benzo-(rst)-pentaphene, resulted in inhibition of tumor development. These data were extended by Haag, et al. who demonstrated that limonene could cause regression of advanced rat mammary carcinomas.

Following in vitro screening, the naturally occurring hydroxylated monocyclic monoterpene POH was chosen for in vivo testing. Dietary POH was greater than five times more potent than limonene at inducing tumor regression. Dietary administration of POH caused 84% regression of rat mammary carcinoma induced by DMBA and 60% regression of rat mammary carcinoma induced by NMU. Limonene and POH are rapidly metabolized in the rat. Rats given a 2% POH diet for 10 weeks had plasma levels of terpene metabolites of 0.82 mM, while those fed a 10% limonene diet for 10 weeks had plasma levels of 0.27 mM. Thus, the difference in potency between limonene and POH may be due to differences in pharmacokinetics. The observed preclinical antitumor effect of perillyl alcohol has not been limited to mammary carcinoma. The laboratory of P. Crowell has observed an antitumor effect of POH in pancreatic carcinoma models. Only the POH-fed hamsters had either regression or no growth of the tumors while control animals showed tumor growth.

The exact mechanism of the antitumor activity of POH has not been established but several potentially important drug-related activities have been observed including: (1) G1 cell cycle arrest and induction of apoptosis; (2) Limonene and POH have been shown to inhibit isoprenylation of a class of 21–26 kD proteins, including small GTP-binding proteins involved in signal transduction, in a dose dependent manner at a point in the mevalonic acid pathway distal to 3-hydroxy-3-methylglutaryl coenzyme A reductase; and (3)

Differential gene regulation including overexpression of the mannose-6-phosphate/insulin-like growth factor II (M6P/IGF II) and transforming growth factor-β (TGF-β) type II receptor genes.

Control and regressing POH-treated mammary carcinomas were examined by immunohistochemical methods and demonstrated increases in levels of both the M6P/IGF II receptor, as well as TGF-β, in treated regressing tumors compared with controls. Consistent with the potential importance of the M6P/IGF II receptor in POH-induced tumor regression, responding tumors had increased M6P/IGF II receptor levels compared to those of treated non-responding tumors. Liver tumors from POH-treated animals showed increased mRNA levels for the M6P/IGF II receptor and for the TGF-β type I, II, and III receptors compared with those of untreated animals. M6P/IGF-II also enhances the activation of TGF-β that acts as a mammary carcinoma mitogenic inhibitor and differentiating factor. In addition, POH inhibits the isoprenylation of small G proteins including ras-p21 that makes association of these proteins with the plasma membrane impossible and thereby inhibits cellular transformation.

BRIEF SUMMARY OF THE INVENTION

In one embodiment, the present invention is a method of sensitizing tumor or carcinoma cells, preferably malignant glioma cells, to radiation. The method comprises the steps of exposing a tumor cell to an effective amount of at least one monoterpene or sesquiterpene, most preferably perillyl alcohol, and irradiating the tumor cell. Thus, the tumor cell will be more sensitive to the irradiation than a control cell that has not been exposed to the monocyclic monoterpene or sesquiterpene.

In another embodiment of the present invention, one sensitizes tumor cells to chemotherapeutic agents by exposing the tumor cell to an effective amount of at least one monoterpene or sesquiterpene and exposing the tumor cell to the chemotherapeutic agent.

In another embodiment of the present invention, one sensitizes tumor cells to immunomodulators, such as cytokines, by exposing the tumor cell to an effective amount of at least one monoterpene or sesquiterpene and exposing the tumor cell to the immunomodulator.

In a most preferred form of the present invention, the tumor cell is a malignant glioma cell and the cell is exposed to perillyl alcohol before and during chemotherapy, radiation or immunomodulation.

It is an object of the present invention to enhance radiation therapy, chemotherapy, and immunomodulator therapy of tumor cells.

It is another object of the present invention to enhance radiation therapy, chemotherapy, and immunomodulator therapy of glioma cells.

Others objects, advantages, and features of the present invention will become apparent to one of skill in the art after review of the specification, claims and drawings.

BRIEF DESCRIPTION OF THE SEVERAL VIEWS OF THE DRAWINGS

FIG. 15A is a graph demonstrating the effect of perillyl alcohol on tumor cell lines. FIG. 15B is a graph demonstrating annexin V staining on POH-treated PC3 cells. FIG. 15C is a graph demonstrating annexin V staining on POH-treated DU145 cells. FIG. 15D is a graph demonstrating the effect of perillyl alcohol on glioma cell lines.

FIG. 16 is a graph demonstrating the effect of perillyl alcohol on the different phases of the cell cycle of tumor cell lines.

FIGS. 17A, B, C and D are a set of four graphs revealing the presence of the membrane-bound form of the Fas ligand on the surface of glioma cells. FIG. 17A demonstrates the results with glioma cell line T98G, FIG. 17B demonstrates the results with glioma cell line U251, FIG. 17C demonstrates the results with glioma cell line U87 and FIG. 17D demonstrates the results with glioma cell line U353.

FIG. 18 is a bar graph showing Fas L and Fas expression in T98G cells following perillyl alcohol treatment.

FIG. 19 is a bar graph demonstrating FasL/Fas in T98G cell line treated with carvone.

FIG. 20 is a bar graph demonstrating FasL/Fas in T98G cell line treated with geranyl tiglate.

FIG. 21 is a bar graph demonstrating FasL/Fas in T98G cell line treated with myrecene.

FIG. 22 is a bar graph demonstrating FasL/Fas in T98G cell line treated with limonene.

FIG. 23 is a bar graph demonstrating FasL/Fas in T98G cell line treated with menthol.

FIGS. 24A and B are graphs illustrating that the cell line under study express some level of the Fas ligand. FIG. 24A demonstrates POH upregulated Fas ligand in tumor cell lines. FIG. 24B demonstrates that perillyl alcohol does not affect Fas receptor in tumor cell lines.

FIG. 25 demonstrates augmentation of CD95 (Fas)-mediated apoptosis.

FIG. 26 is a bar graph demonstrating inhibition of Fas-induced apoptosis by an antagonistic antibody.

FIG. 27 is a bar graph demonstrating induction of cell death in Jurkat cells by POH-treated T98G.

FIG. 28 is a bar graph demonstrating the effect of cisplatin and POH on T98G cells.

FIG. 29 is a bar graph demonstrating the effect of doxorubicin and POH on T98G cells.

DETAILED DESCRIPTION OF THE INVENTION

Figure 1:
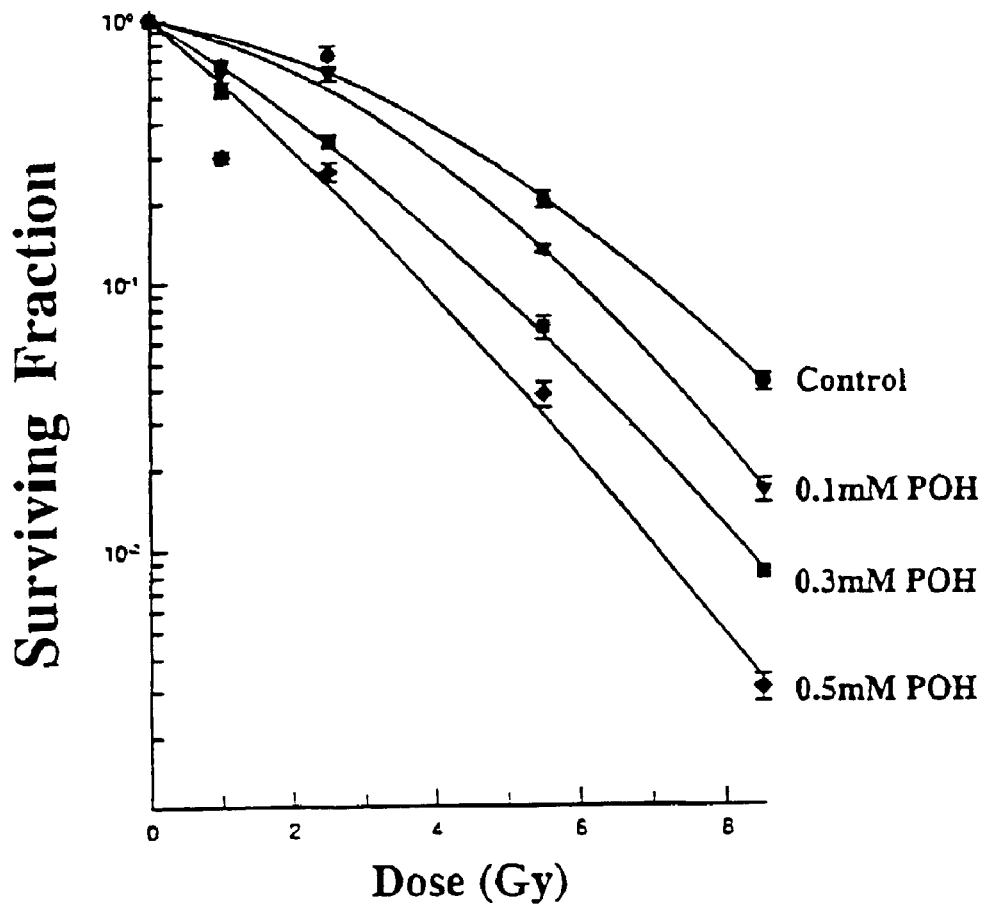
FIG. 1 is a graph of the surviving fraction of T98G glial cells versus dose of POH.

In both clinical situations and in laboratory models, tumor cells have been shown to become resistant to cytotoxic agents. At least in some instances, this is the direct result of alterations within apoptotic pathways such that the normal cellular signals that would ultimately result in programmed cell death are no longer intact. We noted that one of the well-characterized actions of POH is the induction of apoptosis and, at least in some model systems, this effect appears to be tumor cell specific. We therefore hypothesize that the pretreatment of resistant glial cell lines with relatively non-toxic doses of POH would predispose these cells to undergo an apoptotic death after treatment with another cytotoxic agent such as radiation. This hypothesis was the basis of our preliminary experiments. The promising in vivo efficacy of POH, with low toxicity, makes it a promising novel agent to be used in combination with other agents of proven efficacy in the treatment of malignant glioma. This information is potentially important as it could generate insights that would guide the development of both new and novel chemotherapeutic agents and more effective combinations of currently available agents for cancer therapy.

In one embodiment, the present invention is a method of sensitizing tumor or carcinoma cells, such as malignant glioma cells, to radiation comprising the step of exposing the cells to an effective concentration of a monoterpene or sesquiterpene, preferably perillyl alcohol and then exposing the cell to radiation treatment. Other preferred cell lines include prostate, colon and pancreatic cancer cells. The preferred effective dose of terpene is the maximum tolerated dose, preferably 5–15 grams per day. Treatment is preferably before and during irradiation. The monoterpene or sesquiterpene is preferably administered orally and continuously beginning one week prior to the initiation of radiotherapy and continued for two weeks after the completion of radiotherapy. In addition, radiotherapy is preferably scheduled such that one of the daily doses is administered 1–2 hours prior to daily radiotherapy.

The patient is preferably irradiated in a procedure comparable to current tumor irradiation.

Prferred monoterpenes include perillyl alcohol, limonene, carvone, citral, myrecene and geranyl tigllate. Less preferred monoterpenes include menthol.

In another embodiment, the present invention is a method of sensitizing tumor carcinoma cells, such as malignant glioma cells, to chemotherapy. This method comprises the step of exposing the cells to an effective concentration of a monoterpene or sesquiterpene, preferably perillyl alcohol, before or during chemotherapy.

As above, other preferred cell lines include prostate, colon and pancreatic cell lines. The preferred effective dose of terpene is the maximum tolerated dose, preferably 5–15 g/day. Treatment is preferably before and during therapy. Monoterpenes and sesquiterpenes are preferably administered orally and continuously beginning one week prior to the initiation of chemotherapy and continued for two weeks after the completion of chemotherapy. In addition, chemotherapy is preferably scheduled such that one of the daily doses is administered 1–2 hours prior to chemotherapy.

Preferred chemotherapy agents include Cisplatin and Doxorubicin.

Suitable chemotherapeutic agents include those used in cancer therapy, which can be broadly divided into the following families:

Aklylating agents: This group of drugs brings about their action via interaction with bases of DNA. Examples of this class include Nitrogen Mustard, Cholorambucil, Melphalan, Cyclophosphamide, Nitrosourceas, BCNU, CCNU, Procarbazine, Trenimon, Busulphan, Cisplatin and Mitomycin C.

Anti-metabolites: These classes of drugs resemble normal metabolites and compete as substrates for enzyme activity. Examples of this class include Methotrexate (which is an analog vitamin folic acid), 5 fluorouracil (which resembles the thymine and Uracil bases in DNA and RNA respectively), 6 mercaptourines, topothecan, campothecin and its derivatives.

Derivatives of Natural products or chemically synthesized drugs: This group of drugs is heterogeneous and includes the antracyclines Doxorubicin (Adriamycin), Bleomycin, Actinomycin, which have planar structures that can intercalate between the turns of the DNA. The vinca alkaloids (Vincriatine and Vinblastine), which include taxol and the other Taxanes, disrupt mitotic spindle.

Many human malignant diseases have been shown to have alterations in the Fas/FasL ligand pathway. These include but are not limited to malignant glioma, melanoma, breast cancer, prostate cancer and a variety of pediatric malignancies such as neuroblastoma and rhabdomyosarcoma. Cytotoxic systemic chemotherapy is standard in the treatment of these malignancies. The chemotherapeutic agents, which are commonly used, include but are not limited to temadar, mitoxanthrone, cispaltin, adriamycin CPT-11, other derivatives of camptothecin, taxol and other taxanes. All of the aforementioned chemotherapeutic agents have been shown to act through activation of the Fas pathway. In addition, in the process of malignant progression, disruption of the Fas pathway has been shown to result in resistance to these agents. Our laboratory data have shown that the treatment of cancer cells with terepenes and sesquiterpenes, such as perillyl alcohol, results in a restoration of the Fas pathway and results in chemosensitization of that particular cancer cell. The terpene in which the most clinical experience has been obtained is Perillyl alcohol. It has undergone both phase I and phase II testing. It has clearly been demonstrated that patients can maintain a plasma concentration of drug that is in the range in which we have observed our experimental findings. Therefore, preferably, patients would take scheduled perillyl alcohol orally and achieve steady plasma levels of this medication. After which, the patients could then undergo chemotherapy with a particular chemotherapeutic agent. By resulting in restoration of the Fas pathway, the efficacy of the particular chemotherapeutic agent would be expected to be increased.

The present invention is also a method of improving immunomodulatory therapy responds comprising the steps of exposing cells to an effective concentration of a monoterpene or sisquiterpene preferably perillyl alcohol, before or during immunomodulatory treatment. Preferred immunomodulatory agents are cytokines.

Cytokines comprise a family of proteins that include those called Interleukins, lymphokines, monokines, Interfereons, and chemokines. Cytokines are characterized by a short half-life, local (autocrine/paracrine) signaling activity, and rarely systemic signaling. Like polypeptide hormones, cytokines are recognized by specific receptors present on the surface of target cells. In contrast with hormones, however, their targets and effects are highly pleiotropic and redundant.

A number of cytokines have been reported to increase the sensitivity of tumor cell lines to anti-CD95 antibody-mediated apoptosis. IFNγ-has been shown to modulate increase in CD95 and CD95L mRNA as well as protein levels, resulting in apoptosis through the activation of the CD95/CD95L autocrine circuit. IL-18 has been reported to play a potential role in immunoregulation by augmenting the functional activity of FasL on Th1 cells and inducing the synthesis of IFNγ. IL-2 is a T-cell growth factor that has pleiotropic functions in T-cell differentiation, induction of lymphokine-activated killer cells, and regulation of immune responses. IL-2 has been reported to induce FasL/Fas cytotoxicity in a dose-dependent manner. Fas is also up-regulated by IL-1, IL6, or TNF-α pretreatment. One would preferably treat patients with terpenes and immunomodulatory agents in the following manner:

Cytokines are proteins, which are produced by cells and secreted either into the blood stream or into the extra cellular matrix. Cytokines can effect cellular proliferation and in fact trigger cell death under the appropriate circumstances. In fact, a large component of the human immune system by which malignant cells are detected and destroyed is modulated by the production of cytokines. Many cytokines affect the Fas/FasL pathway as well. For example, members of the interferon gamma (IFNγ) family have been shown to cause an induction of the Fas receptor. Interferon gamma has also undergone large phase I and phase II clinical trials. Our data clearly indicate that the terpenes and sesquiterpenes cause an induction of the FasL resulting in at least a partial restoration of the Fas/FasL pathway. The pathway could be further augmented by the pretreatment of patients with a cytokine such as gamma interferon, which causes induction of the Fas receptor. From a clinical point of view, patients could be treated with a scheduled dose of terpene, most likely perillyl alcohol, as this is the terpene with the most clinical experience. This would result in consistent blood levels of this drug resulting in induction of the Fas/L. Simultaneously, the patient could also be treated with an appropriate cytokine, the cytokine of which the most experience is available would be IFNγ. IFNγ has been shown to cause induction of the Fas receptor. As a result, the particular model terpene and the particular cytokine would be expected to have synergistic affects in the restoration of the Fas/FasL pathway. These two agents could also be given in conjunction with a particular chemotherapeutic agent as well.

EXAMPLES

Example 1

T98G Cell Line and POH

Cell Line: The T98G cell line was derived from a resection specimen obtained from a patient with glioblastoma multiforme. T98G cells express endogenous mutant p53 and introduction of wild-type p53 sensitizes these cells to radiation. The radioresistance of this cell line has also been attributed to the presence of high intracellular levels of GSH, which down-regulates NFκB binding activity after exposure to ionizing radiation. A clonogenic survival assay was used to assess the response to treatment in vitro, as it is a measure of reproductive capacity.

Clonogenic Survival Assays: The T98G cell line was obtained from ATCC and maintained in DMEM-F12 medium containing 10% fetal bovine serum, 1% penicillin, streptomycin and 1 mM non-essential amino acids in a humidified incubator at 37° C. Stock solution of POH was made in the medium. One set of plates was treated with graded doses of POH (0.1 mM to 1 mM) for a period of 72 hours. Control dishes were treated with medium alone. All cells were irradiated at a dose rate of 7.5Gy/min using a CS-137 irradiator with single doses ranging from 1 Gy to 8.5Gy. The range of radiation doses used encompasses that used to treat patients.

Following irradiation, both POH treated and untreated cells were harvested by trypsinization and washed with PBS. Cells were incubated for two weeks after initial plating, fixed with methanol, stained with crystal violet and the number of colonies per dish quantitated. Survival was determined as the ratio of plating efficiencies for each irradiated group to that of the unirradiated control.

FIG. 1 graphs radiation-dose cell survival curves for control untreated cultures (●) and cultures treated with increasing concentrations of perillyl alcohol; (▼) 0.1 mM, (■) 0.3 mM, and (□) before and during irradiation. Pretreatment of the % 98G malignant glioma cell line with perillyl alcohol resulted in a dose dependent sensitization of these cells to radiation induced cell death. This result was observed with concentrations as low as 0.1 mM. Pretreatment of malignant glioma cells with 0.5 mM perillyl alcohol showed the most pronounced effect. Radiosensitization was observed at clinically achievable concentrations of perillyl alcohol.

As shown in FIG. 1, the T98G glial cell line is relatively resistant to cell kill by radiation. Pretreatment of T98G cell line with POH, at minimally cytotoxic concentrations, resulted in a dose dependent sensitization of these cells to radiation induced cell death. This effect was seen (with concentrations as low as 0.1 mM POH) in the clinically relevant dose range of POH. Pretreatment of cells with 0.5 mM POH showed the most pronounced radiosensitization.

Example 2

Additional Results with Other Monoterpenes and Cell Lines

Figure 2:
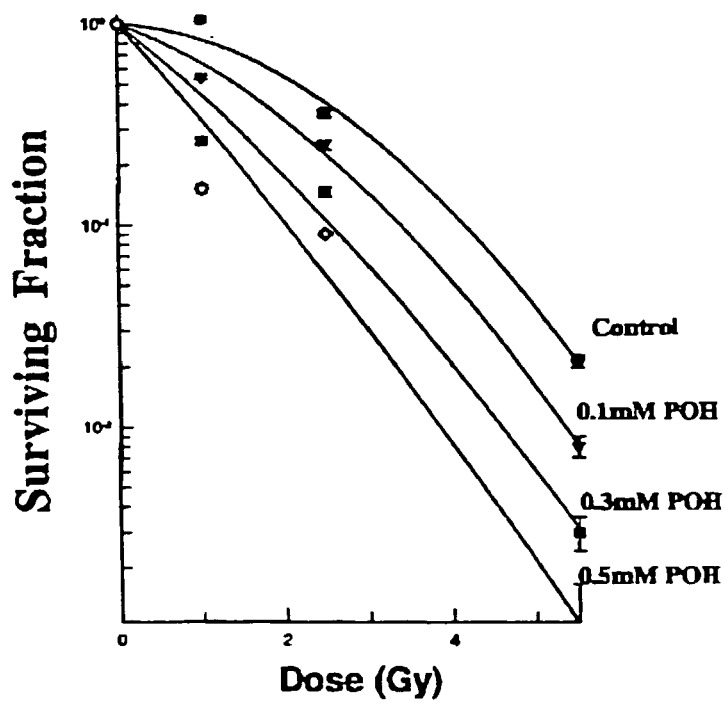
FIG. 2 is a graph demonstrating the effect of perillyl alcohol and radiation on PC3 cells.

FIGS. 2–14 illustrates additional work with other monoterpenes and cell lines. FIG. 2 demonstrates the effect of perillyl alcohol and radiation on PC3 cells. Subconfluent cultures prostate cancer cell line PC3 were treated with 0.1–0.5 mM of POH for 72 hours and subsequently to increasing doses of radiation from 0.1 Gy to 8.5 Gy. Control cells were treated with the indicated doses of radiation alone. The cells were harvested and an optimum number of cells were allowed to growth for 14 days. The resulting colonies were stained and counted. Each graphed point represents mean values ± SE values of triplicate dishes.

Figure 3:
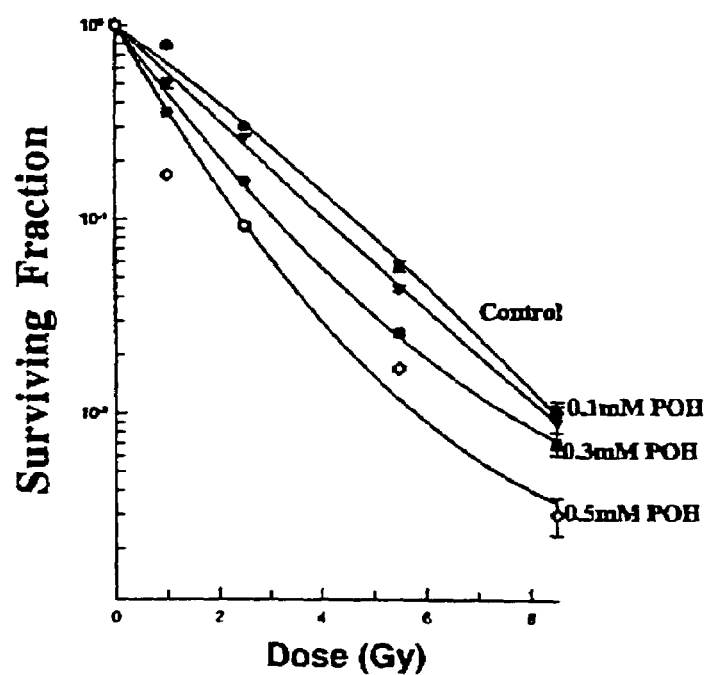
FIG. 3 is a graph demonstrating the effect of perillyl alcohol and radiation on DU145 cells.

FIG. 3 demonstrates the effect of perillyl alcohol and radiation on DU145 cells.

Subconfluent cultures of prostate cancer cell line DU145 were treated with 0.1–0.5 mM of POH for 72 hours and subsequently to increasing doses of radiation from 0.1 Gy to 8.5 Gy. Control cells were treated with the indicated doses of radiation alone. The cells were harvested and an optimum number of cells were allowed to grow for 14 days. The resulting colonies were stained and counted. Each graphed point represents mean values ± SE values of triplicate dishes.

Figure 4:
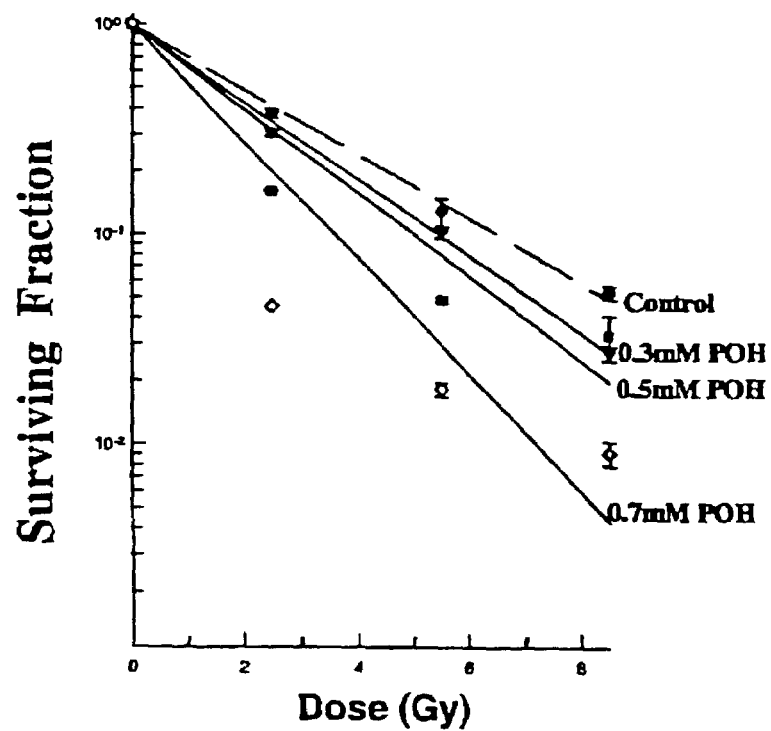
FIG. 4 is a graph demonstrating the effect of perillyl alcohol and radiation on C6 cells.

FIG. 4 demonstrates the effect of perillyl alcohol and radiation on C6 cells. Subconfluent cultures of rat glioma cell line C6 were treated with 0.1–0.5 mM of POH for 72 hours and subsequently to increasing doses of radiation from 0.1 Gy to 8.5 Gy. Control cells were treated with the indicated doses of radiation alone. The cells were harvested and an optimum number of cells were allowed to grow for 14 days. The resulting colonies were stained and counted. Each graphed point represents mean values ± SE values of triplicate dishes.

Figure 5:
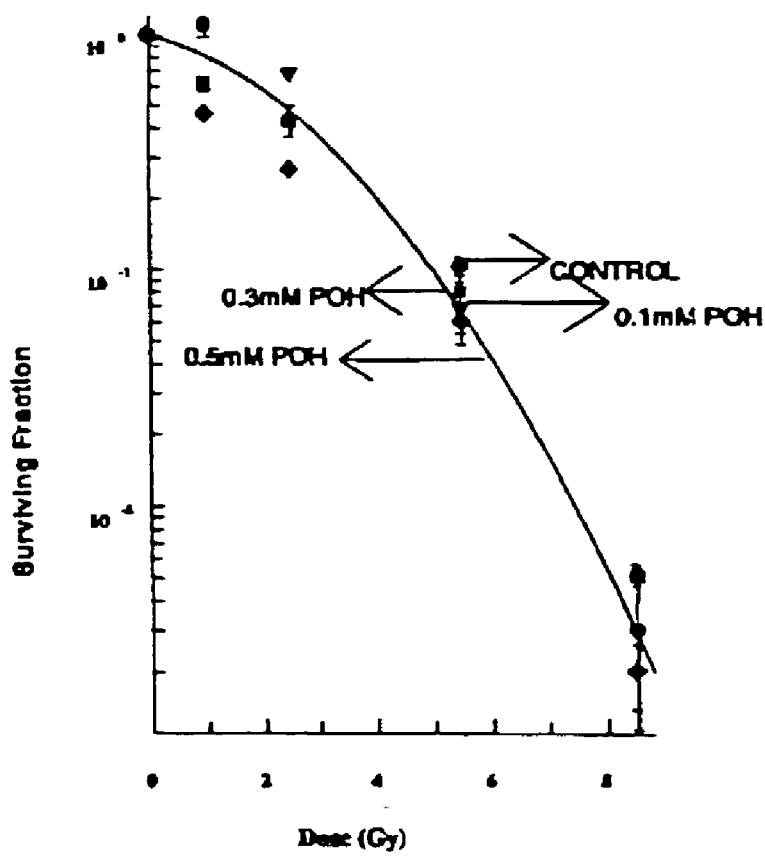
FIG. 5 is a graph demonstrating the lack of radiosensitization in M059K cells.

FIG. 5 demonstrates lack of radiosensitization in M059K cells, cells that were not initially radiation resistant. Subconfluent cultures of human glioma cell line MO 59K were treated with 0.1–0.5 mM of POH for 72 hours and subsequently to increasing doses of radiation from 0.1 Gy to 8.5 Gy. Control cells were treated with the indicated doses of radiation alone. The cells were harvested and an optimum number of cells were allowed to grow for 14 days. The resulting colonies were stained and counted. Each graphed point represents mean values ± SE values of triplicate dishes.

Figure 6:
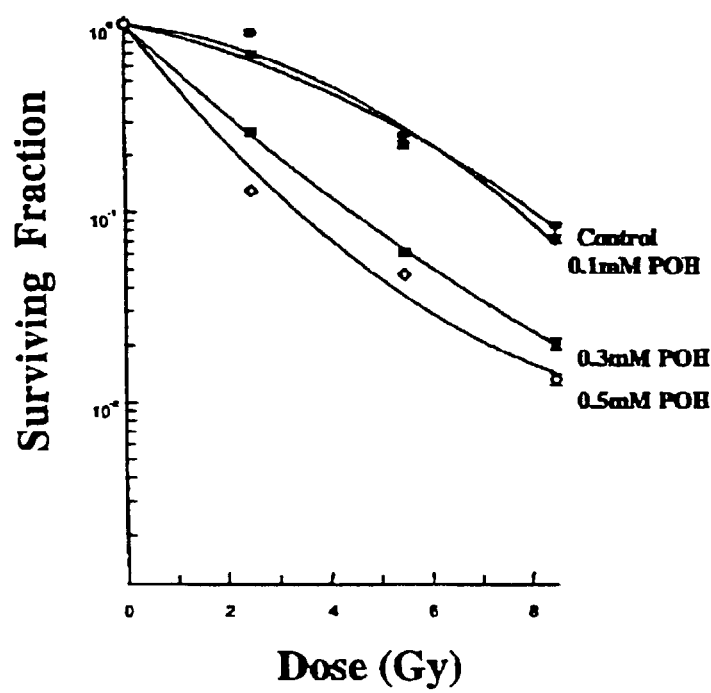
FIG. 6 is a graph demonstrating the effect of perillyl alcohol and radiation on U251 cells.

FIG. 6 demonstrates the effect of perillyl alcohol and radiation on U251 cells. Subconfluent cultures of human glioma cell line U251 were treated with 0.1–0.5 mM of POH for 72 hours and subsequently to increasing doses of radiation from 0.1 Gy to 8.5 Gy. Control cells were treated with the indicated doses of radiation alone. The cells were harvested and an optimum number of cells were allowed to grow for 14 days. The resulting colonies were stained and counted. Each graphed point represents mean values ± SE values of triplicate dishes.

Figure 7:
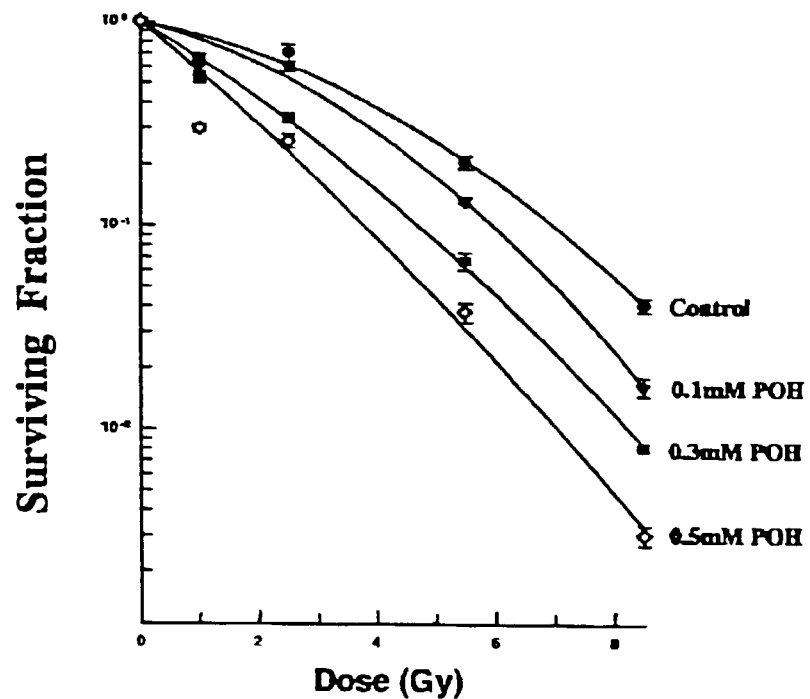
FIG. 7 is a graph demonstrating the effect of perillyl alcohol and radiation on T98G cells.

FIG. 7 demonstrates the effect of perillyl alcohol and radiation on T98G cells. Subconfluent cultures of human glioma cell line T98G were treated with 0.1–0.5 mM of Perillyl Alcohol for 72 hours and subsequently to increasing doses of radiation from 0.1 Gy to 8.5 Gy. Control cells were treated with medium alone. The cells were harvested and an optimum number of cells were allowed to grow for 14 days. The resulting colonies were stained and counted. Each graphed point represents mean values ± SE values of triplicate dishes.

Figure 8:
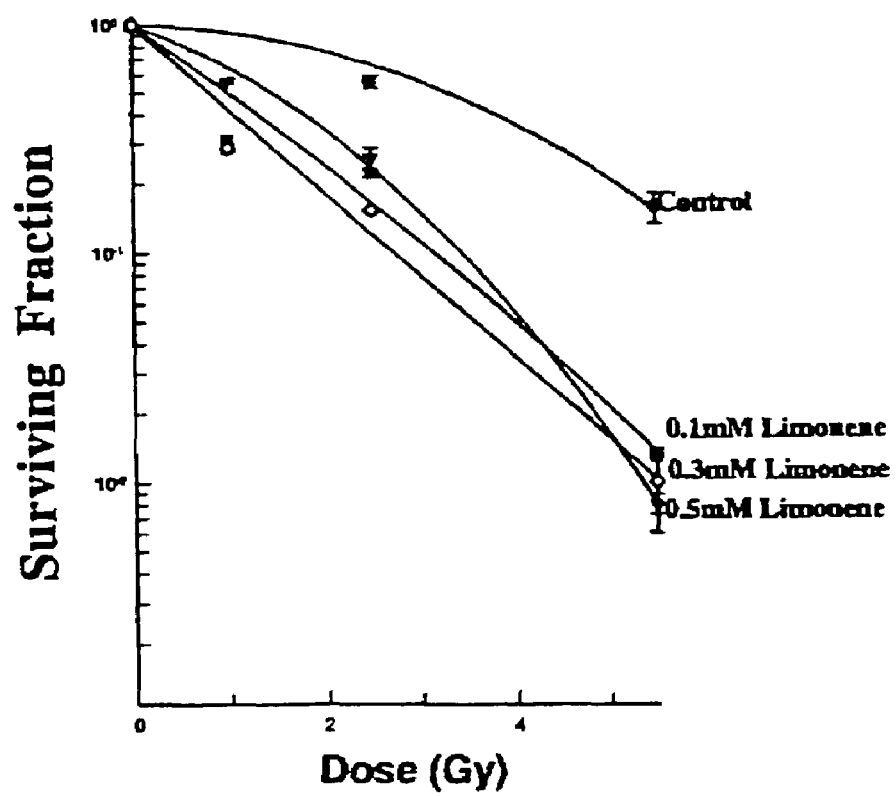
FIG. 8 is a graph demonstrating the effect of limonene and radiation on T98G cells.

FIG. 8 demonstrates the effect of limonene and radiation on T98G cells. Subconfluent cultures of human glioma cell line T98G were treated with 0.1–0.5 mM of Limonene for 72 hours and subsequently to increasing doses of radiation from 0.1 Gy to 8.5 Gy. Control cells were treated with medium alone. The cells were harvested and an optimum number of cells were allowed to grow for 14 days. The resulting colonies were stained and counted. Each graphed point represents mean values ± SE values of triplicate dishes.

Figure 9:
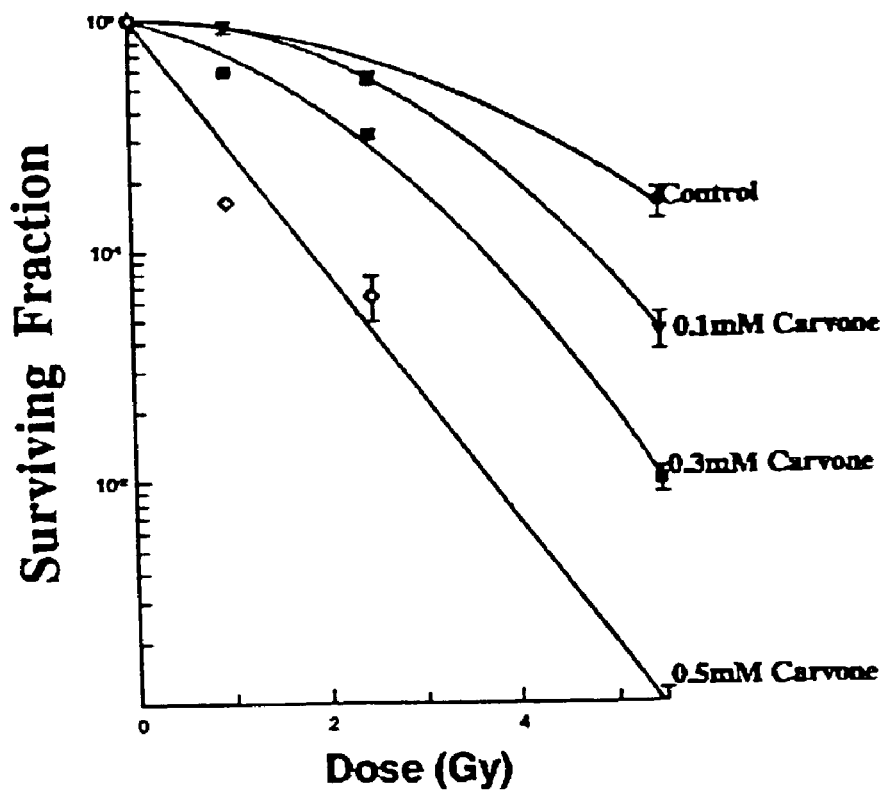
FIG. 9 is a graph demonstrating the effect of carvonel and radiation on T98G cells.

FIG. 9 demonstrates the effect of carvone and radiation of T98G cells. Subconfluent cultures of human glioma cell line T98G, were treated with 0.1–0.5 mM of L-Carvone for 72 hours and subsequently to increasing doses of radiation from 0.1 Gy to 8.5 Gy. Control cells were treated with medium alone. The cells were harvested and an optimum number of cells were allowed to grow for 14 days. The resulting colonies were stained and counted. Each graphed point represents mean values ± SE values of triplicate dishes.

Figure 10:
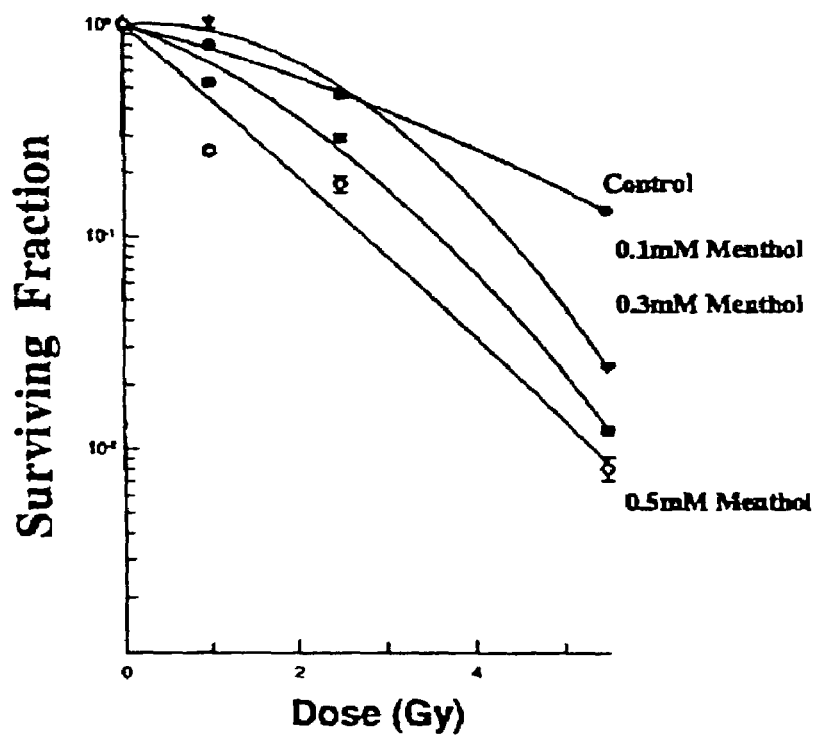
FIG. 10 is a graph demonstrating the effect of menthol and radiation on T98G cells.

FIG. 10 demonstrates the effect of menthol and radiation on T98G cells. Subconfluent cultures of human glioma cell line T98G were treated with 0.1–0.5 mM of Menthol for 72 hours. Control cells were treated with medium alone. The cells were harvested and an optimum number of cells were allowed to grow for 14 days. The resulting colonies were stained and counted. Each graphed point represents mean values ± SE values of triplicate dishes.

Figure 11:
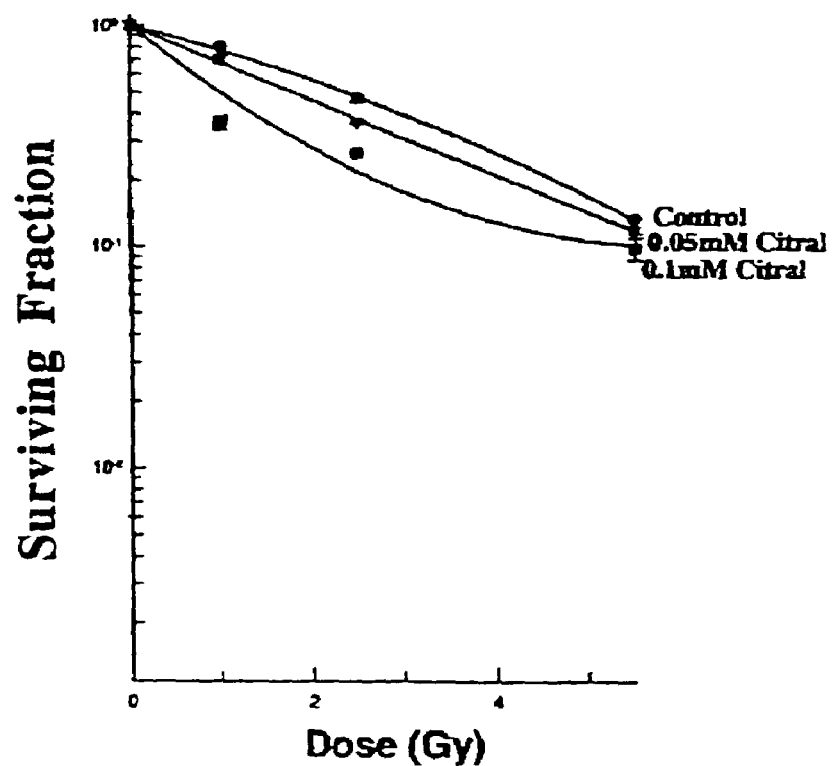
FIG. 11 is a graph demonstrating the effect of citral and radiation on T98G cells.

FIG. 11 demonstrates the effect of citral and radiation on T98G cells. Subconfluent cultures of human glioma cell line T98G, were treated with 0.05 and 0.1 mM of Citral for 12 hours. Control cells were treated with medium alone. The cells were harvested and an optimum number of cells were allowed to grow for 14 days. The resulting colonies were stained and counted. Each graphed point represents mean values ± SE values of triplicate dishes.

Figure 12:
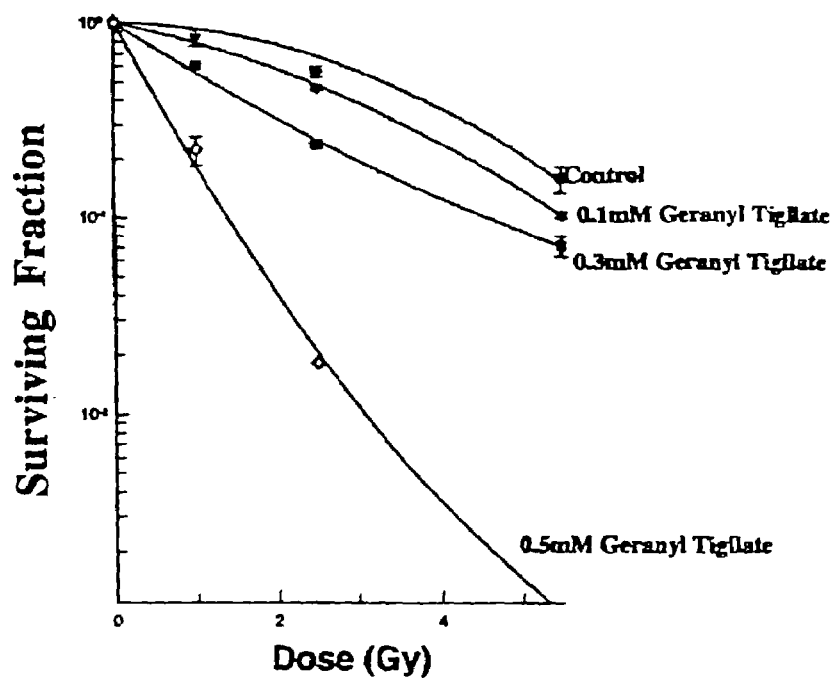
FIG. 12 is a graph demonstrating the effect of tigllate and radiation on T98G cells.

FIG. 12 demonstrates the effect of geranyl tigllate and radiation on T98G cells. Subconfluent cultures of human glioma cell line T98G, were treated with 0.1–0.5 mM of Geranyl Tigllate for 72 hours and subsequently to increasing doses of radiation from 0.1 Gy to 8.5 Gy. Control cells were treated with medium alone. The cells were harvested and an optimum number of cells were allowed to grow for 14 days. The resulting colonies were stained and counted. Each graphed point represents mean values +SE values of triplicate dishes.

Figure 13:
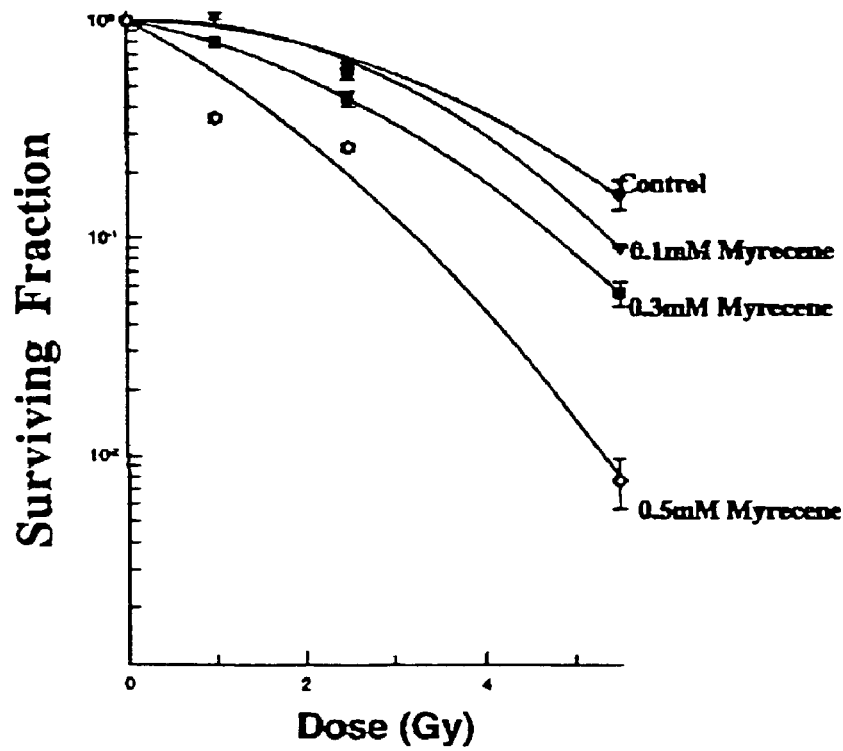
FIG. 13 is a graph demonstrating the effect of myrecene and radiation on T98G cells.

FIG. 13 demonstrates the effect of myrecene and radiation on T98G cells. Subconfluent cultures of human glioma cell line T98G were treated with 0.1–0.5 mM of Myrcene for 72 hours and subsequently to increasing doses of radiation from 0.1 Gy to 8.5 Gy. Control cells were treated with medium alone. The cells were harvested and an optimum number of cells were allowed to grow for 14 days. The resulting colonies were stained and counted. Each graphed point represents mean values ± SE values of triplicate dishes.

Figure 14:
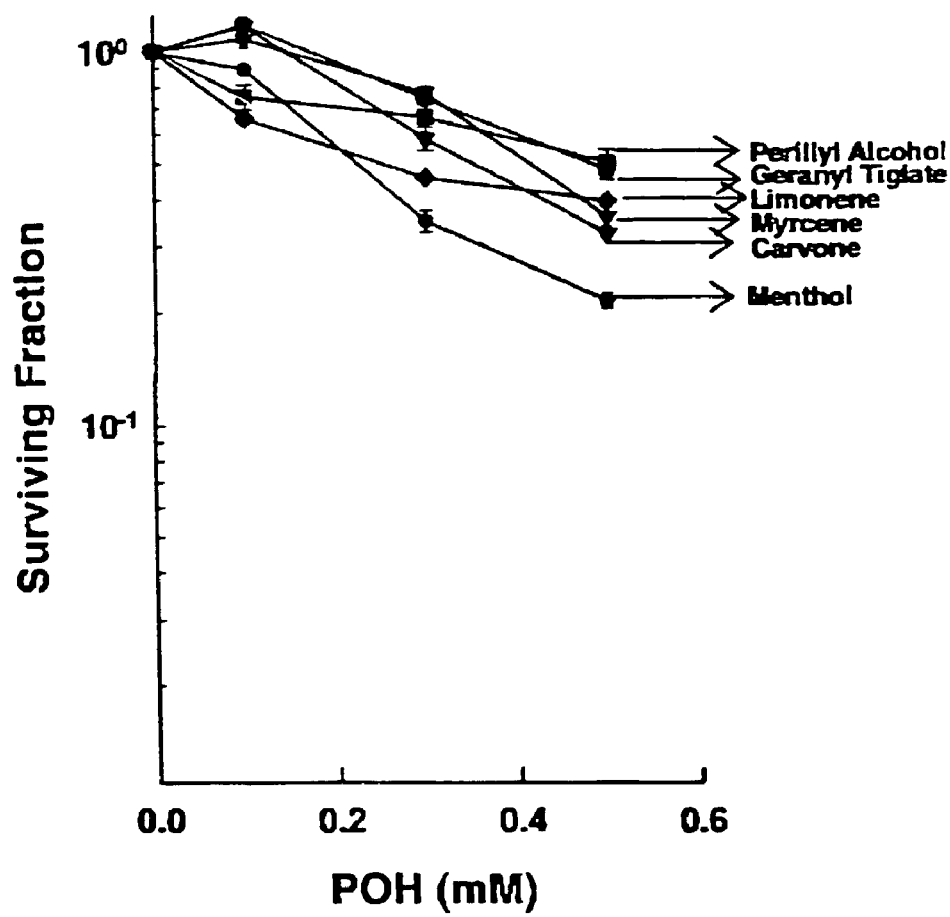
FIG. 14 is a graph demonstrating the effect of monterpenes on glioblastoma cell line T98G.

FIG. 14 demonstrates the effect of various monterpenes on glioblastoma cell line T98G. Subconfluent cultures of human glioma cell line T98G were treated with 0.1–0.5 mM of Perillyl Alcohol, Myrcene, L-Carvone, Geranyl Tigllate, Menthol and Limonene for 72 hours. Control cells were treated with medium alone. The cells were harvested and an optimum number of cells were allowed to grow for 14 days. The resulting colonies were stained and counted. Each graphed point represents mean values ± SE values of triplicate dishes.

Table 1 summarizing data from different cell lines treated with radiation, radiation plus POH, and POH alone. Subconfluent cultures of human glioma (T98G, M059K, U251), prostate (DU145, PC3), colon (DLD-1, HT29) and pancreatic (MIAPACA) cancer cell lines were treated with 0.1–0.5 mM of POH for 72 hours and subsequently to increasing doses of radiation from 0.1 Gy to 8.5 Gy. Control cells were treated with medium alone. The cells were harvested and an optimum number of cells were allowed to grow for 14 days. The resulting colonies were stained and counted. Each graphed point represents mean values ± SE values of triplicate dishes. Percentage survival was determined as the ratio of plating efficiencies for each irradiated group to that of the unirradiated control.

TABLE 1

|  | T98G % SURVIVAL | MO59K % SURVIVAL | U251 % SURVIVAL | MIAPACA % SURVIVAL |
|---|---|---|---|---|
| 5.5 Gy | 0.300 ± 0.009 | 0.111 ± 0.008 | 0.226 ± 0.009 | 0.143 ± 0.296 |
| 0.1 mM POH | 0.755 ± 0.016 | 0.939 ± 0.005 | 1.066 ± 0.200 | 1.503 ± 0.05 |
| 0.3 mM POH | 0.660 ± 0.024 | 0.660 ± 0.020 | 0.397 ± 0.059 | 0.750 ± 0.05 |
| 0.5 mM POH | 0.500 ± 0.006 | 0.623 ± 0.009 | 0.257 ± 0.010 | 0.450 ± 0.07 |

TABLE 1-continued

| | | | | |
|---|---|---|---|---|
| 0.1 mM POH + 5.5 Gy | 0.130 ± 0.002 | 0.061 ± 0.007 | 0.253 ± 0.004 | 0.154 ± 0.018 |
| 0.3 mM POH + 5.5 Gy | 0.066 ± 0.004 | 0.080 ± 0.015 | 0.046 ± 0.005 | 0.059 ± 0.008 |
| 0.5 mM POH + 5.5 Gy | 0.037 ± 0.014 | 0.056 ± 0.006 | 0.019 ± 0.001 | 0.015 ± 0.0027 |

| | DU145 % SURVIVAL | PC3 % SURVIVAL | DLD-1 % SURVIVAL | HT29 % SURVIVAL |
|---|---|---|---|---|
| 5.5 Gy | 0.057 ± 0.0035 | 0.011 ± 0.00147 | 0.114 ± 0.015 | 0.013 ± 0.003 |
| 0.1 mM POH | 0.648 ± 0.008 | 0.734 ± 0.038 | 1.690 ± 0.100 | 1.060 ± 0.090 |
| 0.3 mM POH | 0.456 ± 0.0112 | 0.366 ± 0.017 | 0.899 ± 0.070 | 0.714 ± 0.030 |
| 0.5 mM POH | 0.207 ± 0.005 | 0.244 ± 0.009 | 0.019 ± 0.001 | 0.400 ± 0.010 |
| 0.1 mM POH + 5.5 Gy | 0.044 ± 0.00157 | 0.007 ± 0.0009 | 0.038 ± 0.009 | 0.050 ± 0.005 |
| 0.3 mM POH + 5.5 Gy | 0.026 ± 0.00076 | 0.003 ± 0.0058 | 0.050 ± 0.003 | 0.034 ± 0.003 |
| 0.5 mM POH + 5.5 Gy | 0.017 ± 0.005 | 0.001 ± 0.00067 | 0.001 ± 0.001 | 0.006 ± 0.002 |

Example 3

Effect of Perillyl Alcohol on Tumor Cell Lines

In the present study we evaluated the effect of POH treatment on a panel of human glioma (T98G, MO59K, U-87, U-373, U-251), prostate cancer cell lines (PC3 and DU145), colon (DLD-1, HT29), melanoma (Mel5, M21). Clinically relevant concentrations (0.1 mM–1 mM) of POH appeared to be relatively non-toxic. Higher concentrations of POH (1 mM) resulted in cell death via apoptosis. Referring to FIG. 15A, subconfluent cultures of the indicated glioma (T98G, M059K, U251, U353, U87MG), prostate (DU145, PC3, colon (DLD-1, HT29) and melanoma (Mel5 and M21) cell lines were treated with varying concentrations of POH (0.1 mM–1 mM POH) dissolved in medium. The percent of cells undergoing apoptosis was determined at 72 hours by flow cytometry of propidium iodide (PI) stained cells. The histograms demonstrates the presence of the sub $G_0/G_1$ peak. Each point is an average of duplicate dishes (variation <5%). We conclude that POH induced apoptosis in glioma, prostate, colon and melanoma cell lines. POH treatment at clinically relevant doses (0.1 mM–0.5 mM) appeared to be relatively non-toxic to tumor cell lines, while higher concentrations of POH caused cell death via apoptosis.

FIGS. 15B, 15C and 15D demonstrate perillyl alcohol-induced apoptosis of glioma and prostate cancer cell lines as determined by dual colored (PI and Annexin V) flow cytometry. Glioma (T98G, U251, U353, U87 and MO59K) and prostate (DU145, PC3) cell lines were treated with or without 1 mM perillyl alcohol (POH) for 72 hours. The cells were harvested by trypsinization washed with PBS and subsequently staimed with antibody to annexin V conjugated to FITC and with PI (10 μg/ml). Viable (annexin $V^-/PI^-$) pre-apoptotic (annexin $V^+/PI^-$), apoptotic (annexin $V^{+/PI+}$), and the residual damaged (annexin $V^-/PI^+$) cells were quantitated using this protocol.

As can be seen from FIGS. 15B, C and D, exposure to POH brought about an increase in the percentage of early as well as late apoptotic cells. Each graphed point in the figure represents the average values of duplicate samples. Conclusion: The above staining protocol confirmed the apoptotic mode of cell death in POH treated cells. POH induced apoptosis appeared to be independent of the p53 status as cell lines with wild-type p53 (U87 MG) as well as mutated p53 (T98G, U251, DU145, PC3) responded qualitatively similar to POH treatment as those cell lines.

FIG. 16 demonstrates the effect of perilly alcohol (POH) on cell cycle of tumor cell lines. The indicated glioma (T98G, U251, U87, C6, U353 and MO59K), prostate (DU145 and PC3) melanoma (Mel5 and M21) and colon (DLD-1, HT29) cell lines were treated with medium or with 1 mM of POH dissolved in medium for 72 hours. The cells were harvested, fixed stained with propidium iodide and analyzed by flow cytometry to estimate the various phases of the cell cycle. Each point on the graph represents mean values of duplicate dishes.

Treatment with 1 mM POH induced a block in the $G_2/M$ phase of the cell cycle in all the cell lines except MO59K, where a $G_0/G_1$ block in the cell cycle was observed. The results indicate that POH-induced death was accompanied by a block in the $G_2/M$ phase of the cell cycle.

Example 4

Fas Ligand Expression on Glioma Cells

In the present study POH treatment induced a transient block in the $G_2/M$ or $G_1$ phase of the cell cycle, enhanced the expression of the membrane bound from of the Fas Ligand and sensitized the cells to Fas mediated apoptosis.

The Fas (CD95) and Fas ligand (FasL) are an interacting receptor ligand pair that play a pivotal role in growth regulation, interaction of various tissues with the immune system and elicits apoptosis in many cell types. Cell surface expression of the CD95-L is the major predictor of susceptibility of cells to Fas/APO-1 mediated apoptosis. Faulty regulation of the Fas system has been described in a variety of human tumors with different histogenetic origin.

For as yet unknown reasons, gliomas, prostate lung, pancreas, colon, ovarian cancer, hepatomas cancer have been shown cells co-express CD95 and CD95L in vitro. Several laboratories have reported on the apoptotic potentials of the Fas L by using agonistic anti-Fas antibodies (CH11), which mimics the Fas Ligand.

Recent data from different laboratories have shown that clinically relevant concentrations of drugs widely used in effective chemotherapy as cisplatin, mitomycin C doxorubicin taxol, 5 fluorouracil, teniposide, campothecin, Topo II inhibitors such as etoposide, teniposide, and doxorubicin, which cause DNA damage, activate the Fas receptor Ligand system and to induce apoptosis in malignant cancer cells.

Thus, the intact CD95-CD95L (Fas/FasL) system plays a key role in determining sensitivity or resistance towards anticancer therapy and also provides a new molecular insight into resistance and sensitivity toward chemotherapy in malignancies.

We hypothesize that human tumor cells respond poorly to chemo/radio/immuno-therapy by developing resistance to killing mediated by the Fas-L pathway. Hence, a combination of monoterpenes and sesquiterpenes and a particular chemotherapeutic agent, radiation, or cytokine could potentially overcome this resistance. These studies will define new clinical strategies for targeting chemo/radio resistance observed in a broad spectrum of malignancies that are known to simultaneously express the Fas receptor and Fas Ligand (including glioma, prostate lung, pancreas, colon, ovarian cancer, hepatomas).

We have developed a novel chemo/immunotherapeutic approach for the treatment of cancer that involves the activation of the Fas cascade to increase immunity against cancer cells. The method involves modulation of the Fas Ligand on the tumor cell surface receptors by monoterpenes and sesquiterpenes to increase their sensitivity to apoptotic signals and enhance their susceptibility to Fas mediated apoptosis by chemotherapeutic drugs, radiation as well as by cytotoxic T-lymphocyte (CTL) mediated cytotoxicity.

The method represents a novel chemotherapeutics as well as immunotherapeutic strategy for the treatment of a wide array of cancers having abnormalities in the Fas signaling pathway. Further, this invention provides methods for up regulating the Fas Ligand, and sensitizing cancer cells to Fas mediated apoptosis, thereby stimulating cell-mediated immunity for the prevention, and treatment of tumors of different histogenetic origin having abnormalities in the Fas/Fas Ligand pathway.

Abnormal regulation of Fas/Fas L has been associated to many malignant cancers may be useful for both diagnostic and therapeutic purpose in clinical diagnostics. Determination of Fas (CD-95/APO-1) and its ligand (FasL) has shown relevance for patient survival and could serve as prognostic indicators.

Monoterpenes and sesquiterpenes at non-cytotoxic concentrations could be used to sensitize the tumor cells for physiological apoptosis signals by up regulating the expression of death regulators such as Fas receptor and Ligand; and could be utilized in designing effective treatment modalities.

Monoterpenes and sesquiterpenes could be key players in the apoptosis pathway by bringing about selective killing of cancer cells by anticancer drugs, by immunomodulation of tumor cells and triggering interactions between the tumor cell and the T-cells leading to tumor regression.

Referring to FIG. 17, glioma cell lines (T98G, U251, U87 and U353) were treated with 0.3 mM perillyl alcohol (POH) for 72 hours and the cells were harvested using cell dissociation solution. The resulting cell pellet was stained with biotinylated antibody specific to the human Fas-Ligand (Pharmingen), or IgG1 k isotype control for 45 minutes at 4° C. The cells were washed and incubated with streptavidin conjugated phycoerythrin washed and analyzed by flow cytometry.

The staining protocol described above reveals the presence of the membrane bound form of the Fas ligand on the surface of glioma cell lines and its upregulation is seen as a shift in the histogram following POH treatment.

FIGS. 18–23 demonstrate dual staining of FasL and Fas receptor on T98G cells treated with mono and sesquiterpenes. T98G cells were treated with varying doses (0.1 mM–0.5 mM) of perilly alcohol (FIG. 18), carvone (FIG. 19), geranyl tiglate (FIG. 20), myrecene (FIG. 21), limonene (FIG. 22) and menthol (FIG. 23) for 48 hours in the presence and absence of 5.5 Gy of radiation. The cells were harvested using cell dissociation solution, and the resulting cell pellet was washed and incubated with biotinylated anti-human antibody, which served as a control to eliminate non-specific binding. Following the primary antibody incubation the cells were washed and subsequently stained with secondary antibody conjugated to phycoerythrin (PE) (PharMingen) and antibody to CD95 directly conjugated to allophycocyanin (APC). The stained cells were analyzed using a Beckton-Dickinson FACStar plus and the results were acquired using CELLquest software.

The above staining protocol reveals the presence of the membrane bound form of the Fas Ligand on the surface of T98G cell line and its upregulation following treatment with monoterpenes and sesquiterpenes in the presence and absence of radiation. The Fas receptor was not altered by these treatments.

FIGS. 24A and B demonstrate FasL staining. Subconfluent cultures of the indicated glioma (T98G, U251, U353, U87MG), prostate (DU145, PC3), colon (DLD-1) and melanoma (Mel5) cell lines were treated with varying concentrations of POH (0.1 mM–1 mM POH) dissolved in medium for 72 hours. At the end of the incubation, the cells were harvested using cell dissociation solution, and the resulting cell pellet was washed and incubated with biotinylated anti-human antibody to the FasL (PharMingen) or with an isotype matched anti-human antibody, which served as a control to eliminate non-specific binding. Following the primary antibody incubation, the cells were washed and subsequently stained with secondary antibody conjugated to phycoerythrin (PE) (PharMIngen) and antibody to CD95 directly conjugated allophycocyanin (APC). The stained cells were analyzed using a Beckton-Dickinson FACStar plus and the results were acquired using CELLquest. The cells were harvested using cell dissociation solution.

FIG. 24A shows the upregulation of FasL by POH treatment, while FIG. 24B reveals the lack of upregulation of Fas receptor in the same cell lines except in U87MG.

The results in FIGS. 24A and B illustrate that the cell lines under study expressed some level of the Fas Ligand. POH caused an upregulation of the Fas Ligand. This upregulation was more pronounced at lower concentrations of POH. POH treatment did not alter the levels of the Fas receptor in the same cell lines except U87MG.

Referring to FIG. 25, semiconfluent cultures of glioma and prostate cancel cell lines were treated with the 1 mM POH in the presence or absence of the anti-CD95 antibody CH11 (100 ng/ml), radiation (8.5 Gy for T98G, U87MG, U373 and 5.5 Gy for PC3 and DU145), cycloheximide (CX) or a combination of all for a period of 72 hours. Cells treated with cycloheximide and anti-Fas served as a positive control. The death by treating cells with 1 mM POH or radiation alone was also quantitated. The estimation of apoptosis was done by staining the harvested cells with propidium iodide as described before. Each graphed point in the figure represents the average values of duplicate samples.

POH pretreatment sensitized T98G, U87, U353 and U251 cells to Fas mediated apoptosis even in the absence of cycloheximide. The highest amount of cell death was induced by a combination of POH, radiation and anti-Fas antibody. Thus, upregulation of the FasL by POH sensitized glioma cell lines to Fas-mediated apoptosis.

Referring to FIG. 26, semiconfluent culture plates T98G and U87MG cell lines were treated with the 1 mM POH in the presence or absence of the anti-CD95 antibody CH11 (100 ng/ml), cycloheximide (CX), the Fas-induced apoptosis blocking antibody ZB4 (2 ug/ml) or a combination of all for a period of 72 hours. Viability analysis was carried out using propidium iodide solution by flow cytometric analysis. Each graphed point in the figure represents the average values of duplicate samples.

Both the cell lines appeared to be susceptible to cell death by the Fas antibody in the presence of cycloheximide (CX). This cell death was inhibited by the antagonistic antibody ZB4. POH augmented Fas-mediated apoptosis, in the absence of cycloheximide, which was inhibited in the presence of antagonistic antibody ZB4. The above findings confirm the involvement of the Fas cascade in POH-mediated cell death.

Referring to FIG. 27, subconfluent cells of T98G cells were treated with varying concentrations of perillyl alcohol (0.1 mM–0.5 mM) for 48 hours. At the end of the incubation the media was changed, cells from a Fas-sensitive Jurkat cell line were added to the plate, and the incubation was continued further for 48 hours. At the end of the incubation the target cells (Jurkat) were harvested, washed and the cell viability was assessed. This experiment confirmed that the Fas Ligand expressed on the surface of the glioma cell line T98G was functional as it brought about cell death of a Fas-sensitive Jurkat cell line.

Example 5

Effect of Chemotherapeutic Agents and POH on Glioma Cells

In the present study POH pretreatment brought about significant sensitization to cell kill by chemotherapeutic drugs (Cisplatin, Doxorubicin) in a dose dependent manner in the clinically relevant dose range of the chemotherapeutic drugs.

Referring to FIG. 28, subconfluent cells of T98G cells were treated with varying concentrations of perillyl alcohol (0.1 mM–0.5 mM) for 48 hours and subsequently treated with the indicated dose of cisplatin (0.05 uM–1 uM) for 48 hours. At the end of the treatment, POH pretreated and untreated cells in the presence and absence of cisplatin, were harvested, washed with PBS, plated at the desired cell number and incubated for two weeks. The colonies were stained with crystal violet and quantitated. Survival was determined as the ratio of plating efficiencies for each irradiated group to that of the untreated control.

Pretreatment of T98G cell lines with POH revealed a dose-dependent sensitization of these cells to cisplatin-induced cell death. This effect was seen at relatively non-toxic doses of POH (0.1 mM, 0.3 mM) seen in the clinically relevant dose range of cisplatin.

Referring to FIG. 29, subconfluent cells of T98G cells were treated with varying concentrations of perillyl alcohol (0.1 mM–0.5 mM) for 48 hours and subsequently treated with the indicated dose of doxorubicin (0.01 uM–0.1 uM) for 48 hours. At the end of the treatment, POH-pretreated and untreated cells in the presence and absence of doxorubicin, were harvested, washed with PBS, plated at the desired cell number and incubated for two weeks. The colonies were stained with crystal violet and quantitated. Survival was determined as the ratio of plating efficiencies for each irradiated group to that of the untreated control. Conclusion: Pretreatment of T98G cell lines with POH revealed a dose-dependent sensitization of these cells to doxorubicin-induced cell death. This effect was seen at relatively non-toxic doses of POH (0.1 mM, 0.3 mM) seen in the clinically relevant dose range of doxorubicin. Doxorubicin at concentrations over 0.1 uM appeared to be toxic to the cells.

Example 6

Immunomodulation

Monoterpenes and sesquiterpenes can be used as immunomodulators for drug targeting. Monoterpenes and sesquiterpenes could synergize with cyokines to achieve either an absolute or a relative amplification of the tumoricidal effect of chemotherapeutic drugs or cytokines through activation of the Fas receptor ligand system at the tumor site.

Fas (CD95) is a cell surface protein that mediates rapid apoptosis when cross-linked by antibody or by Fas ligand (FasL). Fas expression is induced by lymphocyte activation, both T- and B-cells and it has been proposed that the increase in Fas expression may provide a means whereby activated cells may be eliminated once they have served their function in the immune response. Exposure to radiation or to other forms of stress, DNA damage may lead to apoptosis not only by increasing surface Fas, but also by affecting intracellular signaling pathways that facilitate Fas-mediated killing.

In effect, the Fas/Fas-L system may serve as a means whereby the immune system can perform a sort of immunological surveillance to identify and eliminate not only activated cells, but also cells that have undergone injury and that require induction of apoptotic death and subsequent elimination.

This system plays a role in the cytotoxic activity of immune cells, the regulation of immune response amplitude and could supplement the direct apoptosis-inducing effects of radiation, heat shock, chemotherapeutic agents, cytokines, and other forms of DNA damage.

We claim:

1. A method of sensitizing tumor cells to chemotherapy, comprising the step of exposing the tumor cell to an effective amount of at least one monoterpene or sesquiterpene and treating the tumor cell with an effective amount of chemotherapeutic agent, wherein the chemotherapeutic agent is selected from the group consisting of alkylating agents, antimetabolites, derivatives of natural products, and chemically synthesized drugs.

2. The method of claim 1 in which the tumor cell is exposed to a monoterpene.

3. The method of claim 2 wherein the monoterpene is perillyl alcohol.

4. The method of claim 2 wherein the monoterpene is selected from the group consisting of perillyl alcohol, limonene, carvone, menthol, citral, myrecene and geranyl tigllate.

5. The method of claim 2 wherein the monoterpene is selected from the group consisting of perillyl alcohol, liminone, carvone, citral, myrecene, and geranyl tigllate.

6. The method of claim 1 wherein the tumor cell is a malignant glioma cell.

7. The method of claim 1 wherein the tumor cell is selected from the group consisting of colon, pancreatic and prostate cells.

8. The method of claim 1 wherein the cell is exposed to the monoterpene or sesquiterpene before and during chemotherapy.

9. The method of claim 1 wherein the cell is exposed to a monoterpene.

10. A method of sensitizing tumor cells to cytokines, comprising the step of exposing the tumor cell to an effective amount of at least one monoterpene or sesquiterpene and treating the tumor cells with the cytokine.

11. The method of claim 10 wherein the monoterpene is perillyl alcohol.

12. The method of claim 10 wherein the monoterpene is selected from the group consisting of perillyl alcohol, limonene, carvone, menthol, citral, myrecene and geranyl tigllate.

13. The method of claim 10 wherein the monoterpene is selected from the group consisting of periulyl alcohol, liminone, carvone, citral, myrecene, and geranyl tigllate.

14. The method of claim 10 wherein the tumor cell is a malignant glioma cell.

15. The method of claim 10 wherein the cell is exposed to the monoterpene or sesquiterpene before or during therapy.

16. The method of claim 15 wherein the cell is exposed to a monoterpene.

17. The method of claim 1 wherein the agent is selected from the group consisting of Nitrogen Mustard, Cholorambucil, Melphalan, Cyclophosphamide, Nitrosourceas, BCNU, CCNU, Procarbazine, Trenimon, Busulphan, Cisplatin and Mitomycin C.

18. The method of claim 1 wherein the agent is selected from the group consisting of Methotrexate, fluorouracil, 6 mercaptourines, topothecan, and campothecin and its derivatives.

19. The method of claim 1 wherein the agent is selected from the group consisting of Doxorubicin (Adriamycin), Bleomycin, Actinomycin, and ymca alkaloids.

20. The method of claim 1 wherein the agent is selected from the group consisting of Cisplatin and Doxorubicin.

* * * * *

UNITED STATES PATENT AND TRADEMARK OFFICE
CERTIFICATE OF CORRECTION

PATENT NO. : 7,056,491 B2
APPLICATION NO. : 10/014724
DATED : June 6, 2006
INVENTOR(S) : Michael N. Gould et al.

It is certified that error appears in the above-identified patent and that said Letters Patent is hereby corrected as shown below:

Column 4, Line 4 "M059K" should be -- MO59K --.

Column 5, Line 44 "Prferred" should be -- Preferred --.

Column 9, Line 4 "M059K" should be -- MO59K --.

Column 10, Line 46 "M059K" should be -- MO59K --.

Column 11, Line 30 "M059K" should be -- MO59K --.

Claim 13: Column 17, Line 6 "periulyl" should be -- perillyl --.

Claim 19: Column 18, Line 10 "ymca" should be -- vinca --.

Signed and Sealed this

Twenty-sixth Day of December, 2006

JON W. DUDAS
*Director of the United States Patent and Trademark Office*